United States Patent
Schmitt et al.

(10) Patent No.: US 11,793,462 B2
(45) Date of Patent: Oct. 24, 2023

(54) INTRAVASCULAR MEASUREMENT AND DATA COLLECTION SYSTEMS, APPARATUS AND METHODS

(71) Applicant: LightLab Imaging, Inc., Westford, MA (US)

(72) Inventors: Joseph M. Schmitt, Cupertino, CA (US); Chenyang Xu, Medford, MA (US)

(73) Assignee: LightLab Imaging, Inc., Westford, MA (US)

(*) Notice: Subject to any disclaimer, the term of this patent is extended or adjusted under 35 U.S.C. 154(b) by 491 days.

(21) Appl. No.: 15/913,300

(22) Filed: Mar. 6, 2018

(65) Prior Publication Data
US 2018/0192957 A1    Jul. 12, 2018

Related U.S. Application Data

(63) Continuation of application No. 12/455,523, filed on Jun. 2, 2009, now abandoned.
(Continued)

(51) Int. Cl.
*A61B 5/00* (2006.01)

(52) U.S. Cl.
CPC .......... *A61B 5/6852* (2013.01); *A61B 5/0066* (2013.01); *A61B 5/7264* (2013.01)

(58) Field of Classification Search
CPC .... A61B 5/0066; A61B 5/6852; A61B 5/7264
See application file for complete search history.

(56) References Cited

U.S. PATENT DOCUMENTS

| 5,054,492 A | 10/1991 | Scribner et al. |
| 5,321,501 A | 6/1994 | Swanson et al. |

(Continued)

FOREIGN PATENT DOCUMENTS

| CN | 106361295 | 2/2017 |
| CN | 107730540 | 2/2018 |

(Continued)

OTHER PUBLICATIONS

Jeon et al.; A feasibility study of optical coherence tomography for guiding deep brain probes; Journal of Neuroscience Methods vol. 154, Issues 1-2, Jun. 30, 2006, Available online Feb. 9, 2006; pp. 96-101 (Year: 2006).*

(Continued)

*Primary Examiner* — Chao Sheng
(74) *Attorney, Agent, or Firm* — Lerner David LLP

(57) ABSTRACT

A method and apparatus for determining properties of a tissue or tissues imaged by optical coherence tomography (OCT). In one embodiment the backscatter and attenuation of the OCT optical beam is measured and based on these measurements and indicium such as color is assigned for each portion of the image corresponding to the specific value of the backscatter and attenuation for that portion. The image is then displayed with the indicia and a user can then determine the tissue characteristics. In an alternative embodiment the tissue characteristics is classified automatically by a program given the combination of backscatter and attenuation values.

20 Claims, 22 Drawing Sheets
(8 of 22 Drawing Sheet(s) Filed in Color)

Related U.S. Application Data

(60) Provisional application No. 61/058,077, filed on Jun. 2, 2008.

(56) References Cited

U.S. PATENT DOCUMENTS

| | | |
|---|---|---|
| 5,459,570 A | 10/1995 | Swanson et al. |
| 5,465,147 A | 11/1995 | Swanson |
| 5,488,674 A | 1/1996 | Burt et al. |
| 5,509,093 A | 4/1996 | Miller et al. |
| 5,531,227 A | 7/1996 | Schneider |
| 5,662,109 A | 9/1997 | Hutson |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,920,390 A | 7/1999 | Farahi et al. |
| 5,956,355 A | 9/1999 | Swanson et al. |
| 5,989,189 A | 11/1999 | LeBlanc et al. |
| 5,999,588 A | 12/1999 | Shao et al. |
| 6,013,033 A | 1/2000 | Berger et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,208,883 B1 | 3/2001 | Holupka et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,608,717 B1 | 8/2003 | Medford et al. |
| 6,706,004 B2 | 3/2004 | Tearney et al. |
| 6,879,851 B2 | 4/2005 | McNamara et al. |
| 6,891,984 B2 | 5/2005 | Petersen et al. |
| 7,061,622 B2 | 6/2006 | Rollins et al. |
| 7,148,970 B2 | 12/2006 | de Boer |
| 7,208,333 B2 | 4/2007 | Flanders et al. |
| 7,241,286 B2 | 7/2007 | Atlas |
| 7,414,779 B2 | 8/2008 | Huber et al. |
| 7,415,049 B2 | 8/2008 | Flanders et al. |
| 7,593,559 B2 | 9/2009 | Toth et al. |
| 7,625,366 B2 | 12/2009 | Atlas |
| 7,668,342 B2* | 2/2010 | Everett .............. G06T 7/0014 |
| | | 356/482 |
| 7,729,746 B2 | 6/2010 | Redel et al. |
| 7,787,129 B2 | 8/2010 | Zysk et al. |
| 8,953,911 B1 | 2/2015 | Xu et al. |
| 8,983,580 B2 | 3/2015 | Boppart et al. |
| 2002/0115931 A1 | 8/2002 | Strauss et al. |
| 2003/0028100 A1 | 2/2003 | Tearney et al. |
| 2004/0068192 A1* | 4/2004 | Westphal ............... A61B 3/102 |
| | | 600/476 |
| 2004/0215166 A1 | 10/2004 | Atlas |
| 2005/0004453 A1 | 1/2005 | Tearney et al. |
| 2005/0201662 A1 | 9/2005 | Petersen et al. |
| 2005/0238067 A1 | 10/2005 | Choi |
| 2006/0058622 A1 | 3/2006 | Tearney et al. |
| 2006/0095065 A1 | 5/2006 | Tanimura et al. |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0227286 A1 | 10/2006 | Hong et al. |
| 2006/0241461 A1 | 10/2006 | White et al. |
| 2006/0241465 A1 | 10/2006 | Huennekens et al. |
| 2006/0241487 A1* | 10/2006 | Nair ......................... A61B 8/12 |
| | | 600/467 |
| 2006/0241503 A1 | 10/2006 | Schmitt et al. |
| 2006/0244973 A1 | 11/2006 | Yun et al. |
| 2007/0081236 A1 | 4/2007 | Tearney et al. |
| 2007/0115481 A1 | 5/2007 | Toth et al. |
| 2007/0123771 A1 | 5/2007 | Redel et al. |
| 2007/0167710 A1* | 7/2007 | Unal ..................... A61B 5/0066 |
| | | 600/407 |
| 2007/0260198 A1 | 11/2007 | Atlas |
| 2008/0069776 A1 | 3/2008 | Yamamoto et al. |
| 2008/0100612 A1 | 5/2008 | Dastmalchi et al. |
| 2008/0161696 A1 | 7/2008 | Schmitt et al. |
| 2008/0165366 A1 | 7/2008 | Schmitt et al. |
| 2008/0177183 A1* | 7/2008 | Courtney ................. A61B 8/12 |
| | | 600/463 |
| 2009/0079993 A1 | 3/2009 | Yatagai et al. |
| 2010/0094127 A1 | 4/2010 | Xu |
| 2016/0058622 A1 | 3/2016 | Allred |
| 2018/0192957 A1 | 7/2018 | Schmitt et al. |
| 2019/0110776 A1 | 4/2019 | Yu et al. |

FOREIGN PATENT DOCUMENTS

| | | |
|---|---|---|
| CN | 106377229 | 4/2019 |
| GB | 2408797 A | 6/2005 |
| JP | H04-189349 A | 7/1992 |
| JP | H09-070404 A | 3/1997 |
| JP | H11-173976 A | 7/1999 |
| JP | 2002534199 A | 10/2002 |
| JP | 2006000385 A | 1/2006 |
| JP | 2006516739 A | 7/2006 |
| JP | 2007029520 A | 2/2007 |
| JP | 2008069107 A | 3/2008 |
| JP | 2008-510586 | 4/2008 |
| JP | 2008510586 A | 4/2008 |
| JP | 2008510595 A | 4/2008 |
| JP | 2011-173976 | 9/2011 |
| WO | 2004 066824 | 8/2004 |
| WO | 2006 024015 | 3/2006 |
| WO | 2006076409 | 7/2006 |
| WO | 2007002685 | 1/2007 |
| WO | 2007015051 A2 | 2/2007 |
| WO | 2007 028531 | 3/2007 |
| WO | 2007028531 A1 | 3/2007 |
| WO | 2007060973 A1 | 5/2007 |
| WO | 2008024419 A1 | 2/2008 |

OTHER PUBLICATIONS

Image segmentation—Wikipedia (Year: 2020).*
Boyer et al.; Automatic recovery of the optic nervehead geometry in optical coherence tomography; published on May 1, 2006; IEEE Transactions on Medical Imaging (vol. 25, Issue: 5, May 2006); pp. 553-570 (Year: 2006).*
Xu et al., "Characterization of atherosclerosis plaques by measuring both backscattering and attenuation coefficients in optical coherence tomography," Journal of Biomedical Optics, vol. 13(3), May/Jun. 2008, 8 pages.
Kholodnykh et al., "Accurate Measurement of Total Attenuation Coefficient of Thin Tissue with Optical Coherence Tomography," IEEE Journal on Selected Topics in Quantum Electronics, vol. 9, No. 2, Mar./Apr. 2003, pp. 210-221.
Schmitt et al., "Optical-coherence tomography of a dense tissue: statistics of attenuation and backscattering," Phys. Med. Biol. 39 (1994), pp. 1705-1720.
Notification of Transmittal of the International Search Report and the Written Opinion of the International Searching Authority for International Patent Application No. PCT/US2009/046035, 15 pages.
Japanese Office Action for Patent Application No. 2011-511907 dated Sep. 24, 2013 (9 pages).
English translation of Office Action of Japan Patent Office for Japanese Patent Application No. 2015-112641 dated Jun. 6, 2017 (3 pages).
P. Gatenby. "Neural networks, Part I: Feedforward Hardlimited Networks," 2002 http://www.hpcc.org/datafile/V21N1/neural1.html (8 pages).
Van der Meer et al., "Localized Measurement of Optical Attenuation Coefficients of Atherosclerotic Plaque Constituents by Quantitative Optical Coherence Tomography," 2005, IEEE Transactions on Medical Imaging, vol. 24, No. 10, pp. 1369-1376.

(56) References Cited

OTHER PUBLICATIONS

Mehrotra et al., "Elements of Artificial Neural Networks," 1997, Massachusetts Institute of Technology, pp. 24-27.
Search Report by Registered Search Organization for Japanese Application No. 2014-011005 dated Nov. 19, 2014. 10 pgs.
Search Report by Registered Search Organization for Japanese Application No. 2011-511907 dated Sep. 13, 2012. 18 pgs.

* cited by examiner

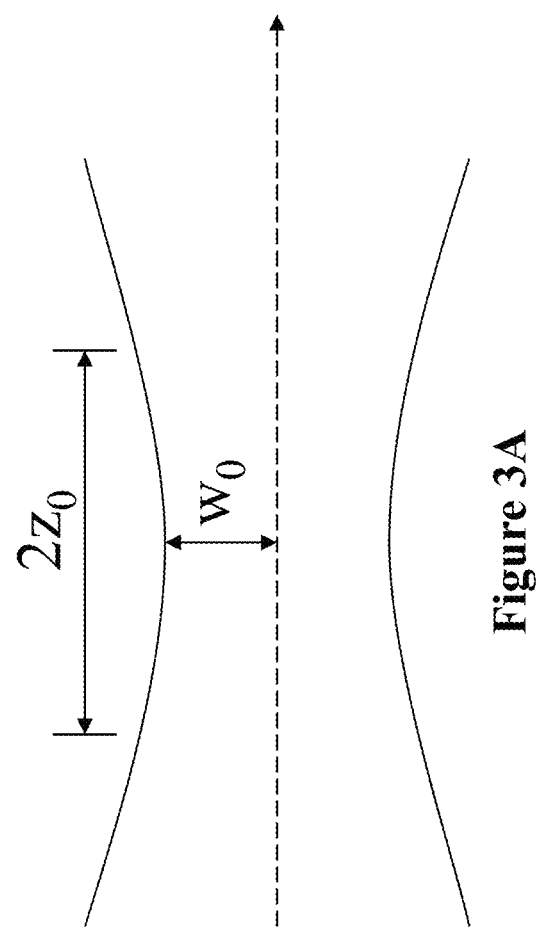

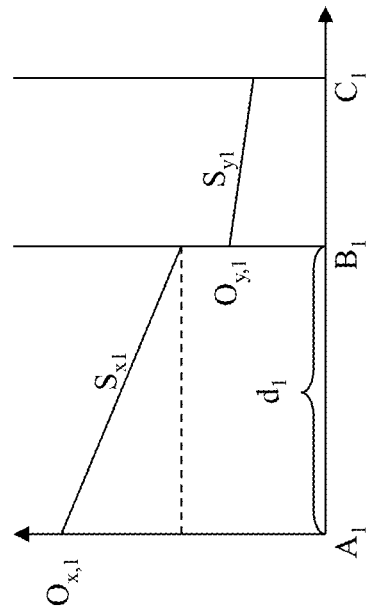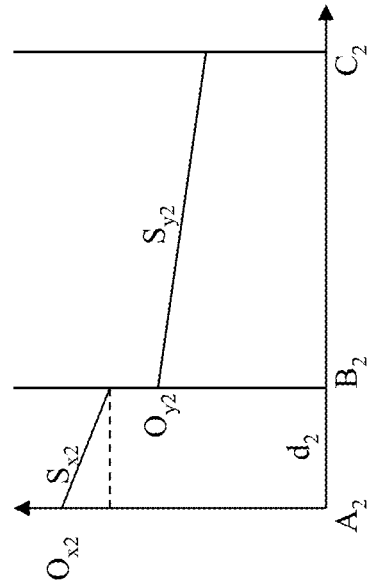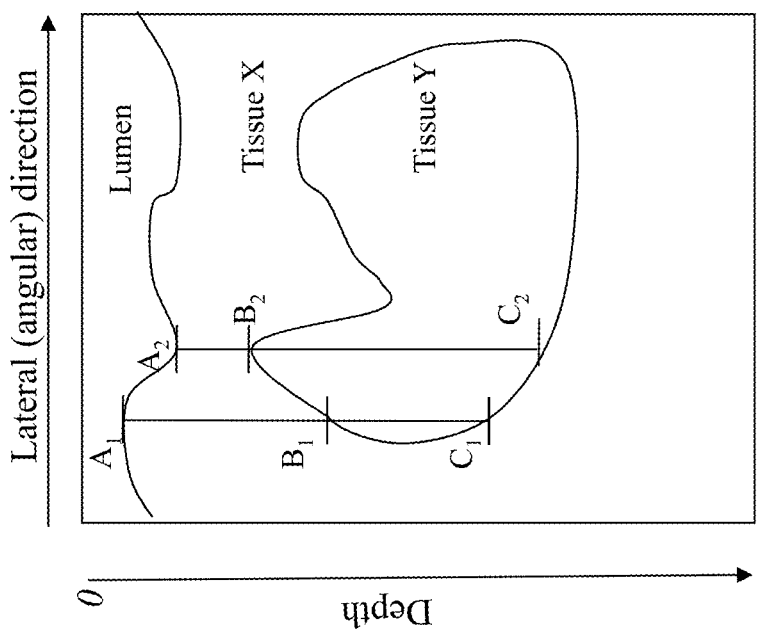
Figure 10B
Figure 10C
Figure 10A

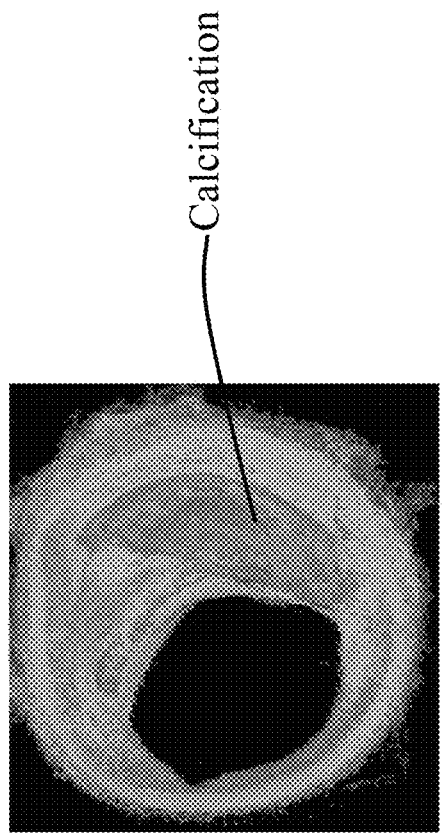
Calcification
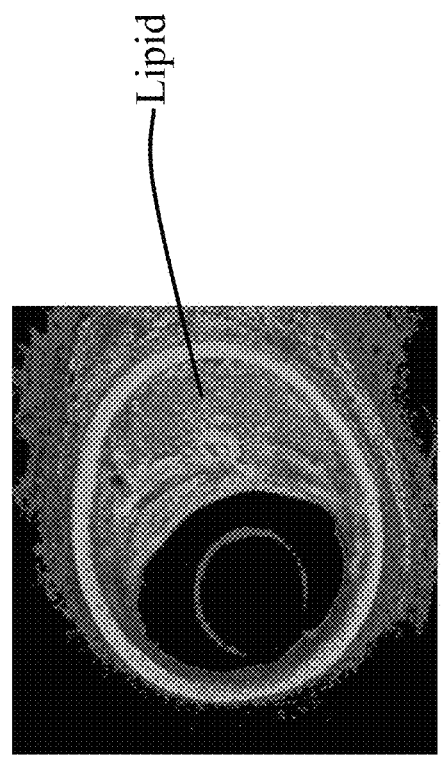
Lipid
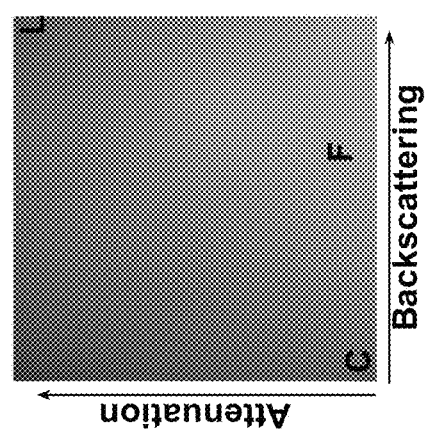
Figure 11B
Combination
Figure 11C

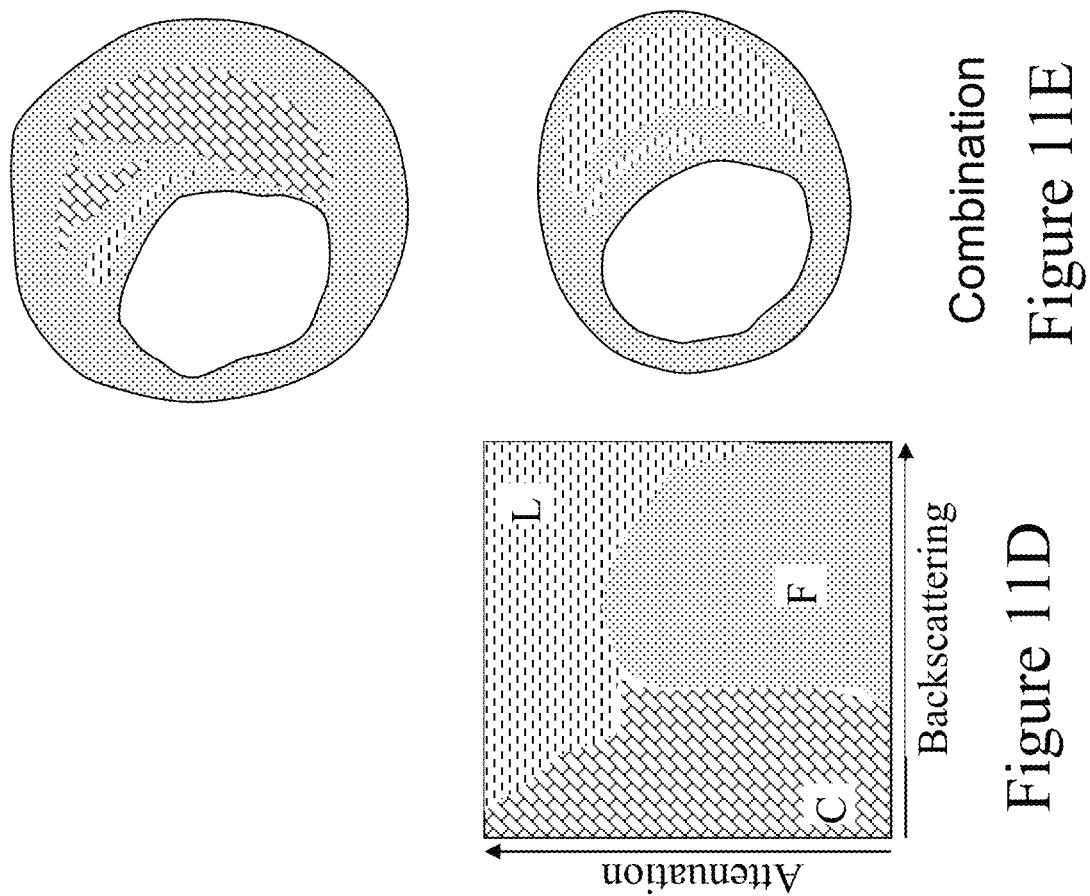
Figure 11D  Figure 11E Combination

INTRAVASCULAR MEASUREMENT AND DATA COLLECTION SYSTEMS, APPARATUS AND METHODS

CROSS-REFERENCE TO RELATED APPLICATIONS

This application is a continuation of U.S. patent application Ser. No. 12/455,523, filed on Jun. 2, 2009, which claims priority from U.S. Provisional Patent Application No. 61/058,077, filed on Jun. 2, 2008, the disclosures of which are incorporated by reference herein in their entirety.

RELATED APPLICATIONS

This application claims priority to U.S. Provisional Application 61/058,077 filed on Jun. 2, 2008, the disclosure of which is herein incorporated by reference in its entirety.

FIELD OF INVENTION

This invention provides methods for tissue characterization using optical coherence tomography. Specifically, in part, such characterization can be performed by measuring a tissue's optical and image properties.

BACKGROUND

Optical coherence tomography (OCT) is an interferometric imaging technique with widespread applications in ophthalmology, cardiology, gastroenterology and other fields of medicine. The ability to view subsurface structures with high resolution (2-15 μm) through small-diameter fiber-optic probes makes OCT especially useful for minimally invasive imaging of internal tissues and organs. OCT systems can generate images up to 100 frames per second, making it possible to image coronary arteries in the beating heart artery within a few seconds. OCT can be implemented in both time domain (TD-OCT) and frequency domain (Fourier domain OCT or optical frequency domain imaging, OFDI).

OCT imaging of portions of a patient's body provides a useful tool for doctors to determine the best type and course of treatment. For example, imaging of coronary arteries by intravascular OCT may reveal the location of a stenosis, the presence of vulnerable plaques, or the type of atherosclerotic plaque. This information helps cardiologists choose which treatment would best serve the patient-drug therapy (e.g., cholesterol-lowering medication), a catheter-based therapy like angioplasty and stenting, or an invasive surgical procedure like coronary bypass surgery. In addition to its applications in clinical medicine, OCT is also very useful for drug development in animal and clinical trials.

Normal arteries have a consistent layered structure consisting of intima, media and adventia. As a result of the process of atherosclerosis, the intima becomes pathologically thickened and may contain plaques composed of different types of tissues, including fiber, proteoglycans, lipid and calcium, as well as macrophages and other inflammatory cells. These tissue types have different optical properties that can be measured by OCT. The plaques that are believed to be most pathologically significant are the so-called vulnerable plaques that have a fibrous cap with an underlying lipid pool.

In a typical OCT imaging system, an optical probe mounted on a catheter is carefully maneuvered to a point of interest such as within a coronary blood vessel. The optical beams are then transmitted and the backscattered signals are received through coherent detection using an interferometer. As the probe is scanned through a predetermined line or area, many data lines can be collected. An image (2D or 3D) is then reconstructed using well-known techniques. This image is then analyzed visually by a cardiologist to assess pathological features, such as vessel wall thickening and plaque composition.

Since tissue type is identified by its appearance on the screen, errors may occur in the analysis because certain information (such as tissue type) cannot be readily discerned. The standard OCT image only contains the intensity information of the OCT signals. Small changes in the optical properties that influence the OCT signals cannot be readily discerned. Thus, it would be advantageous to have an OCT system and method to measure the optical properties and use them to aid scientists and clinicians. The present invention addresses this need.

SUMMARY OF THE INVENTION

The methods are explained through the following description, drawings, and claims.

In general the invention relates to a method and apparatus for determining properties of a tissue or tissues imaged by OCT. In one embodiment the backscatter and attenuation of the OCT optical beam is measured and based on these measurements an indicium, such as color, is assigned for each portion of the image corresponding to the specific value of the backscatter and attenuation for that portion. The image is then displayed with the indicia and a user can then determine the tissue characteristics. Alternatively, the tissue characteristics can be classified automatically by a program given the combination of backscatter and attenuation values.

In one aspect the invention relates to a method for identifying tissue components in situ. In one embodiment the method comprises the steps of: taking an OCT image of a tissue in situ; measuring the attenuation and backscatter at a point in the OCT image; and determining the composition of the tissue at a location in the tissue corresponding to the point in the OCT image in response to the measured attenuation and backscatter. In another embodiment the method further comprises mapping a pair of coordinates in backscatter-attenuation space to an indicium of the value of the pair of coordinates in the backscatter-attenuation space. In one embodiment the indicium is a color. In another embodiment the method further comprises displaying the indicium corresponding to the measured attenuation and backscatter at the point in the OCT image.

In another aspect the invention relates to a system for identifying tissue components in situ. In one embodiment the system comprises an OCT subsystem for taking an OCT image of a tissue in situ; a processor in communication with the OCT subsystem for measuring the attenuation and backscatter at a point in the OCT image and determining the composition of the tissue at a location in the tissue corresponding to the point in the OCT image in response to the measured attenuation and backscatter; and a display for displaying the OCT image and an indicium corresponding to the measured attenuation and backscatter at the point in the OCT image.

In another aspect the invention relates to a processor-implemented method for identifying tissue components in situ. In one embodiment, the method includes the steps of (a) collecting an OCT dataset of a tissue sample in situ using a probe; (b) measuring an attenuation value and a backscattering value at a point in the tissue sample; and (c) determining a tissue characteristic at a location in the tissue sample corresponding to an image location in an OCT image formed from the OCT dataset in response to the measured attenuation value and backscattering value. The method can include the further step of mapping a pair of coordinates in backscatter-attenuation space to an indicium of the value of the pair of coordinates in the backscatter-attenuation space. The method can include the further step of displaying the indicium corresponding to the measured attenuation and backscatter at the point in the OCT image. The tissue characteristic can be selected from the group consisting of cholesterol, fiber, fibrous, lipid pool, lipid, fibrofatty, calcium nodule, calcium plate, calcium speckled, thrombus, foam cells, and proteoglycans. The indicium can be, for example, a color. The indicium can also be selected from the group consisting of an over-lay, a colormap, a texture map, and text. The method can include the further step of classifying tissue type using a property selected from the group consisting of backscattering, attenuation, edge sharpness, and texture measurements. The method can include the further step of correcting a focusing effect to improve tissue type classification. The method can include the further step of applying angular intensity correction to account for an attenuation effect, such as, for example, a blood-related attenuation effect. The method can include the further step of determining a tissue characteristic using a technique selected from the group consisting of boundary detection, lumen location, and OCT location depth.

In another aspect the invention relates to a system for identifying tissue components in situ. In one embodiment, the system includes (a) an OCT subsystem for taking an OCT image of a tissue in situ; (b) a processor in communication with the OCT subsystem for measuring the attenuation and backscatter at a point in the OCT image and determining a tissue characteristic of the tissue at a location in the tissue corresponding to the point in the OCT image in response to the measured attenuation and backscatter; and (c) a display for displaying the OCT image and an indicium corresponding to the measured attenuation and backscatter at the point in the OCT image. The tissue characteristic can be selected from the group consisting of cholesterol, fiber, fibrous, lipid pool, lipid, fibrofatty, calcium nodule, calcium plate, calcium speckled, thrombus, foam cells, and proteoglycans.

In another aspect the invention relates to an optical coherence tomography system for identifying tissue characteristics of a sample. In one embodiment the computer system includes a detector configured to receive an optical interference signal generated from scanning a sample and converting the optical interference signal to an electrical signal; an electronic memory device and an electronic processor in communication with the memory device and the detector. The memory device can include instructions that, when executed by the processor, cause the processor to: analyze the electrical signal and generate a plurality of datasets corresponding to the sample, wherein one of the plurality of datasets comprises backscattering data; compare the backscattering data to a first threshold, the backscattering data mapping to a first location in the sample; and if the backscattering data exceeds the first threshold, characterize the first location in the sample as having a first tissue characteristic. In some embodiments, the processor is further caused to generate an OCT image of the sample such that the first tissue characteristic is identified and displayed relative to the first location. The first tissue characteristic can be selected from the group consisting of cholesterol, fiber, fibrous, lipid pool, lipid, fibrofatty, calcium nodule, calcium plate, calcium speckled, thrombus, foam cells, and proteoglycan. In some embodiments, at least one of the plurality of datasets includes OCT scan data, attenuation data, edge sharpness data, texture parameters, or interferometric data.

BRIEF DESCRIPTION OF THE DRAWINGS

The patent or application file contains at least one drawing executed in color. Copies of this patent or patent application publication with color drawings will be provided by the Office upon request and payment of the necessary fee.

The objects and features of the invention can be better understood with reference to the drawings described below, and the claims. The drawings are not necessarily to scale, emphasis instead generally being placed upon illustrating the principles of the invention. In the drawings, numerals are used to indicate specific parts throughout the various views. The drawings associated with the disclosure are addressed on an individual basis within the disclosure as they are introduced.

FIG. 3A shows optical properties, geometric information and parameters for a beam of electromagnetic waves used to collect OCT data.

FIG. 5A shows the image before denoising and FIG. 5B shows the same OCT image after the application of the denoising method.

FIG. 10A is a diagram of a section of lumen wall showing the interaction of the beam at two locations with the various tissues in the wall.

FIGS. 10B and 10C are schematic diagrams that illustrate the dimensions and variables used in a method of extracting attenuation/backscattering coefficients from a multi-layered tissue object shown in FIG. 10A according to an embodiment of the invention.

FIG. 11B shows a color-map plot of attenuation and backscattering data suitable for implementing a method for distinguishing different tissue properties according to an embodiment of the invention.

FIG. 11C shows two exemplary OCT images depicting different tissue properties that have been enhanced using the color-map shown in FIG. 11B.

FIGS. 11D-11E show hatched versions of FIGS. 11B and 11C.

DETAILED DESCRIPTION

Figure 1:
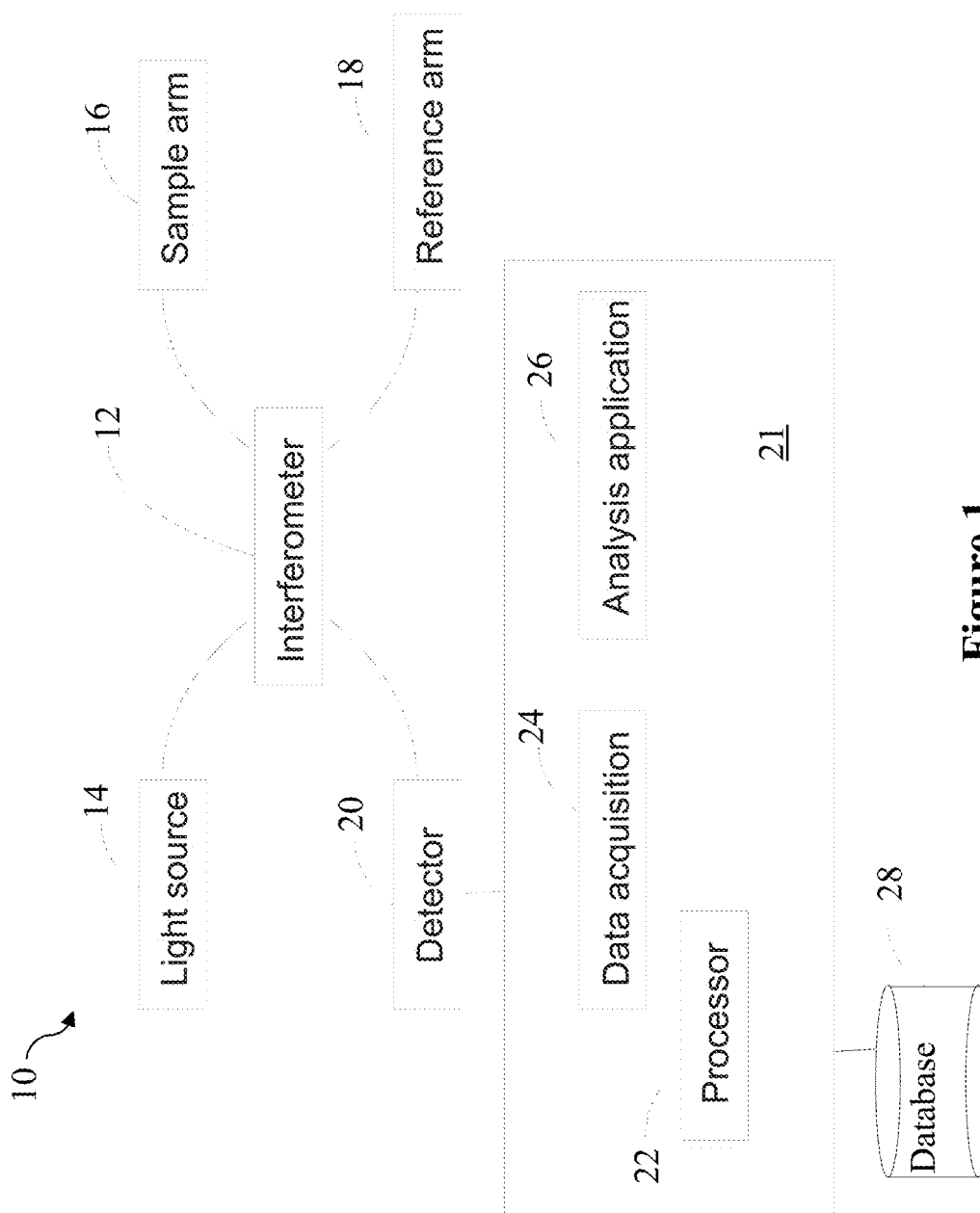
FIG. 1 is a schematic view of a generalized OCT data acquisition system in accordance with an embodiment of the invention.

The following description refers to the accompanying drawings that illustrate certain embodiments of the invention. Other embodiments are possible and modifications may be made to the embodiments without departing from the spirit and scope of the invention. Therefore, the following detailed description is not meant to limit the invention. Rather, the scope of the invention is defined by the appended claims.

In general, the invention relates to methods for tissue characterization of vessel walls using optical methods based on what is generally termed low coherence interferometry (LCI), such as, but not limited to optical coherence tomography (OCT) whether in the time or Fourier domain. The methods described herein solve the problems encountered in semi-automatic or automatic tissue characterization application such as optical calibration, artifact removal, generating accurate optical and spatial parameter measurement from regions of interests, tissue segmentations, and statistical discriminant analysis of tissue types. As used herein discriminant analysis refers to classifying images or data into different classes.

The present invention provides methods for analyzing OCT data and images to characterize biological tissues. Although methods described herein may pertain specifically to vascular tissues, the methods also apply to tissues in other organs of the body, including tissues in the gastrointestinal, pulmonary, and reproductive tracts. Embodiments of the present invention operate in conjunction with an OCT system and a computing device that include characterization software and a decision database as discussed below with respect to FIG. 1. Specifically, the OCT console and OCT probe are used to acquire raw OCT data and demodulated data from a blood vessel. In this context, demodulated data refers to OCT images, such as grayscale images, or the underlying data associate with such images. The OCT data is received by the computing device such as a processor and used to create an OCT image on which numerical, text or graphical information about tissue characteristics are displayed.

In part, embodiments of the invention are used to evaluate the walls of certain lumens and tissues accessible by an OCT probe. Exemplary tissue images or tissue data sets can include, but are not limited to plaques, lipid pools, and stent placement zones. Typically, histology images of a sample are used to automate an OCT data-based characterization of the same and unrelated samples. In one embodiment of the present invention, reference data (e.g., normal tissue type data from histology reviewed samples) are characterized or generated using software comparisons with data stored in a database. In one embodiment, the characterization software implements some or all of the steps shown in FIG. 12A. However, this software can implement other methods as appropriate and discussed herein.

In general, one embodiment of the characterization software is based on manual selection of regions-of-interest in a histology image. The actual histology data is evaluated to identify different tissue types. In turn, these identified tissue evaluations are be compared to OCT images obtained with respect to the same sample tissue. By comparing the manually identified tissues and structures of interest in the histology images, training sets are created to allow some of the software and programming logic described herein to automatically characterize tissue types and structures in an OCT image. For example, if tissue layer A is identified in the histology image, the same region of interest A' can be identified in the corresponding OCT image. This process can be repeated to build a database of information used to locate different tissues in an OCT image. Backscattering and attenuation data can be used as outlined below to facilitate this process. Other embodiments of the methods described herein also include image preprocessing steps (such as focus correction), and optical property measurement.

As part of an exemplary sample measurement session, one or more tissue samples are first interrogated using OCT such that OCT scan data is collected. Once the scan data is processed, the resulting OCT images relating to the tissue samples are calibrated and corrected for imaging artifacts. Next, the tissue sample is cross-sectioned to create a histology image designating different parts of the image as composed of different elements or features. The tissue samples are processed using a histological method (such as dye staining), and digitized to create a histology image or histology data set.

In one embodiment, the OCT images are image mappings of the backscattered signal that reaches the OCT probe after being reflected from the OCT scan of the sample. In one embodiment, the histology images are digitized microscopic images of real tissue sample undergone dye staining, i.e., the histology images are color images showing the dye distribution. Since the dyes bind to certain molecules and tissue types preferentially, the histology images map the molecules/tissue types in a tissue sample. As used herein, a histology image typically includes data regarding tissue or a tissue structure or the image created from such underlying data.

The histology image allows operators to identify tissue types (or characterizations) and regions of interest (ROIs). The OCT images are matched or mapped to the histology image. In one embodiment, the mapping is done manually. Next, the characterization software then identifies a corresponding region on the OCT image. The characterization software then calculates at least one of the tissue optical properties or spatial features, the result of which is stored in the database. Statistical analysis is then applied to form a discriminant analysis method using both the OCT data and the tissue types identified in histology.

FIG. 1 is a schematic illustration of a generalized view of an OCT imaging system 10. The imaging system typically includes an interferometer 12 and an optical source 14, for example, a broadband light source, or a wavelength-swept source that provides optical beam to both sample arm 16 and reference arm 18. The sample arm 16 delivers the optical beam to tissue through an optional scanning apparatus such as an OCT probe. In one embodiment, the optical scanning apparatus is a rotational transducer attached to the end of the sample arm and is carefully maneuvered through the patient's body to the region of interest. The scanning probe provides a substantially collimated beam to the vessel walls. The reference arm has a built-in known reflector, which may be located either at a separate optical path or at a common path as sample arm but at a slightly different location. The backscattered light signals from both the sample arm and the reference arm are recombined at the optical interferometer 12.

The combined optical interference signal is converted to electrical signal by the optical detector (or detector arrays) 20. The signal is then used to construct images. The detector is in electrical communication with a processing and analysis subsystem 21 in one embodiment. The subsystem can include a processor 22, a data acquisition module 24, and an analysis software application 26.

The processor 22 is a portion of a computer system or other processor-based device executes various software programs or program logic such as data acquisition 24 and data analysis modules 26. In other embodiments the acquisition and analysis system elements are hardware modules. In one embodiment, the software includes characterization software and graphic user interface for displaying regions of interest as described below. Typically, the processor 22 is in communication with memory (not shown) and a database 28. The database is used to store all types of data and participate in various processing phases and stages as outlined below.

OCT is currently the most widespread variant of this group of imaging systems. The sample arm of commercially available OCT system has many configurations, including microscope, forward-looking endoscope and side-looking endoscope. To simplify description without loss of generalization, OCT with side-looking endoscope is used as a non-limiting example for describing this invention below. In this configuration, an optical probe is mounted in an endoscopic catheter at the sample arm 16. The substantially collimated beam exits from the optical probe mounted on the side. Typically the catheter and the probe are rotated to generate 2D scan and can also be pulled or advanced while rotating to generate 3D scan.

The OCT signal can be described as the light collected from a discrete light imaging volume. Signals from discrete locations within the sample include the image data set. The signal detected from any location is determined by the scattering element's size, refractive indices, density, geometrical arrangement, in addition to characteristics of the optical imaging system. Since different tissues have different chemical composition and microscopic structure, their appearances differ in OCT images. Qualitative differences in appearance have been used clinically for identifying and characterizing plaques. However, this qualitative approach requires extensive experience and is prone to instrumental and human errors. To assist in tissue characterization, the present invention provides various means to incorporate quantitative measurements. In some embodiments, this tissue characterization is performed automatically using the processor 22 and characterization software.

In one embodiment of the invention, the characterization software inputs the OCT data, calibrates the signal strength, enhances data quality via filtering, corrects imaging artifacts, and calculates parameters for all tissue regions or specific regions of interest identified by operators, and uses the parameters stored in database to identify tissue type or characterization. In this embodiment, the characterization software identifies at least one of the tissue optical properties or spatial features from OCT data. The tissue optical properties are calculated and displayed. The individual tissue optical properties are displayed either individually or in combination.

To calculate the optical parameters of the tissue, many optical models can be used. In one embodiment of the present invention, the optical parameters of the tissue can be extracted by fitting the data based on single-scatterer theory. In another embodiment of the present invention, the optical parameters can be extracted by models, such as the extended Huygens-Fresnel (ELF) theory that include multiple-scatterer effect.

In one the embodiment, discussed below, P(z) is the power of OCT signal received. According to single-scattering theory, the OCT signal power P(z) collected from a homogeneous sample, from depth $z_0$ to $z_1$ is described by:

$$P(z) = KA(z,\phi)T(z_0)\mu_b \exp(-2\mu_a z), z_0 < z < z_1$$

$$\log[P(z)] = \log[KA(z,\phi)T(z_0)] + \log(\mu_b) - 2\mu_a z, z_0 < z < z_1 \quad (1.1)$$

where z is the depth into the sample, K is the delivered incident power, $A(z, \phi)$ is the optical system efficiency, $T(z_0)$ is the optical transmission efficiency from tissue surface to depth $z_0$, $\mu_b$ is the tissue backscattering coefficient, and $\mu_a$ is the tissue attenuation coefficient. In $A(z, \phi)$, the angular dependence $\phi$ arises from varying beam delivering efficiency caused by catheter rotation and blood attenuation. The z dependence is caused by factors such as the divergent beam focusing profile. The tissue back-scattering coefficients and the attenuation coefficients are characteristic of tissue types and are the principal optical parameters used in certain embodiments to determine the tissue characteristics. For a specific imaging setting, the K value and $A(z, \phi)$ value are constant. For a specific region of interest, the $T(z_0)$ is also a constant. However, there can be variations from these constants in some embodiments. Given a substantially constant behavior for the different parameters discussed above, a linear relationship between log [P(z)] and the depth z is a reasonable assumption. Accordingly, a line can be fit to the data describing the relationship between scan depth and the signal received by the OCT system. This linear model has various uses. For example, based on this linear model, the attenuation coefficient can be calculated from the slope of the fitted line; while the backscattering coefficient can be calculated from the offset of the fitted line.

Figure 3B:
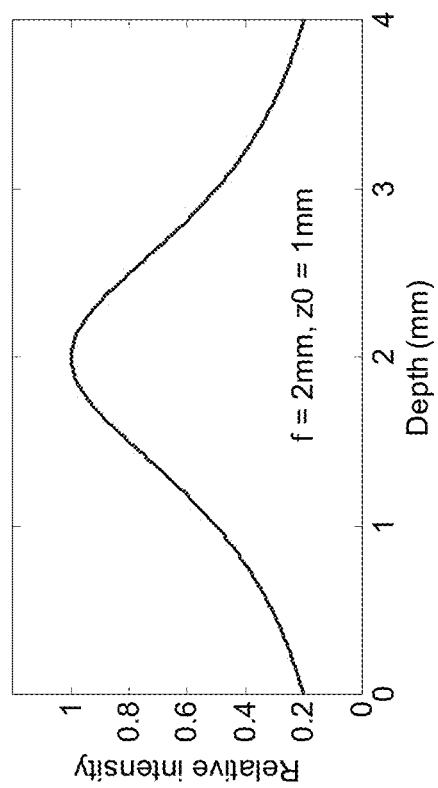
FIGS. 3B and 3C show plots of relative intensity and gain, respectively, as a function of beam distance from the probe tip used to perform OCT data collection according to an embodiment of the invention.

With respect to the depth parameter, the z dependence is illustrated by FIGS. 3A and 3B as discussed below. In turn, the z-dependence can be resolved using a model fit to the data shown in FIG. 3C. The ϕ dependence has many influencing factors that can be addressed using certain techniques. In one embodiment, the ϕ dependence is resolved using a model fit to the data of FIG. 4B as described below.

Figure 2:
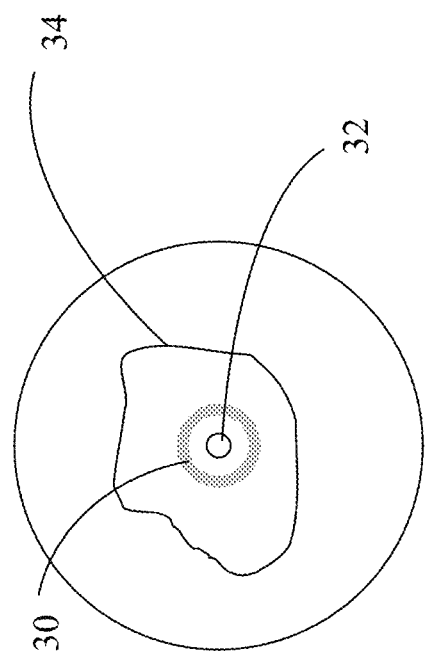
FIG. 2 is a schematic view of a cross-section of a lumen with an imaging probe disposed therein with a semi-transparent layer according to an embodiment of the invention.

The OCT imaging machine and sample arm beam delivery device has various optical efficiencies. To ensure the accurate measurement of tissue optical properties, in addition to noise subtraction and filtering, the imaging system must be carefully calibrated and various artifacts must be removed. As shown in FIG. 2, to calibrate the light intensity exiting the sample probe, one embodiment of this calibration method places a semi-transparent layer of materials 30, having a known backscattering coefficient, around the optical probe 32. In the figure shown, both are disposed in a lumen of interest 34.

The OCT intensity from this layer 30 is proportional to light intensity exiting the probe, thereby providing a calibrated optical reference. This semi-transparent layer 30 can be in the form of outer sheath of the catheter, a layer between the outmost sheath and the optical fiber probe, or a specific semi-transparent coating on the optical fiber, the catheter sheath or other structural layers in between that has calibrated reflection coefficients. In order to consider this embodiment in more detail, it is useful to review the components of an exemplary OCT probe.

In one embodiment, the OCT probe is composed of the rotating optical fiber 32 surrounded by one or more layers of plastic or glass. These constitute a substantially stationary protective sheath. The partial reflector can be either layer 30 (which is a part of the sheath), or an interface inside the optical fiber or GRIN lens assembly. The advantage of using layer 30 is that the intensity of layer 30 is generally visible in the OCT images. The disadvantage of layer 30 is that it is a larger and more complex structure. This greater size and complexity may be non-uniform and the overall layer may have a rotational dependence. One advantage of using the interface as the reflector is that it rotates together with the fiber. Hence, it does not suffer potential rotational dependence. The disadvantage of the interface is that it may lie outside the normal OCT scan range (i.e. proximal to the fiber tip, where the normal OCT image range begins just distal to the fiber tip) requiring the OCT scan range to adjusted inward to capture this interface and losing a commensurate portion of the outer scan region.

The partial reflector 30 is used to calibrate the delivered incident light intensity (K). Partial reflecting layer 30 can be calibrated by injecting a laser of known intensity and recording the reflected signal strength.

An electromagnetic beam such as an optical beam suitable for performing OCT scans is shown in FIG. 3A, where $w_0$ is the beam waist and $z_0$ is the Rayleigh range. Due to finite wavelength, the optical beam used in the imaging is a Gaussian beam which is divergent from the beam waist. It produces a beam focusing profile that can be described by the Lorentzian function.

$$A(z) \propto \frac{z_0^2}{z_0^2 + (z-f)^2} \tag{1.2}$$

Figure 3C:
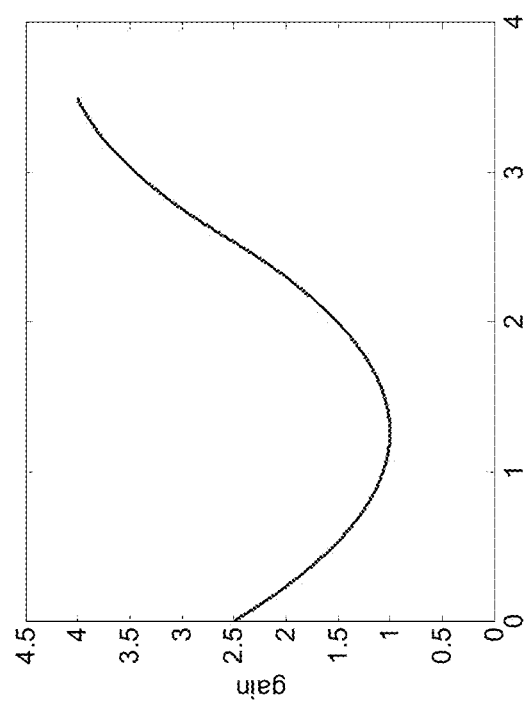

In equation 1.2, A(z) is light intensity at depth z, $z_0$ is the Rayleigh range, and f is the focal length of the lens assembly. In a homogeneous media, the divergent beam profile produces an OCT intensity pattern that peaks at the focal plane, and rolls off from either side, as shown in FIG. 3B. To correct for the loss of intensity due to defocus, the focal length of the imaging probe is measured and the inverse of equation (1.2) is applied to OCT signal P(z). To suppress excessive boosting of noise in regions far away from the focus plane, the amplification factor is limited far from the focusing point as shown in FIG. 3C.

Figure 4A:
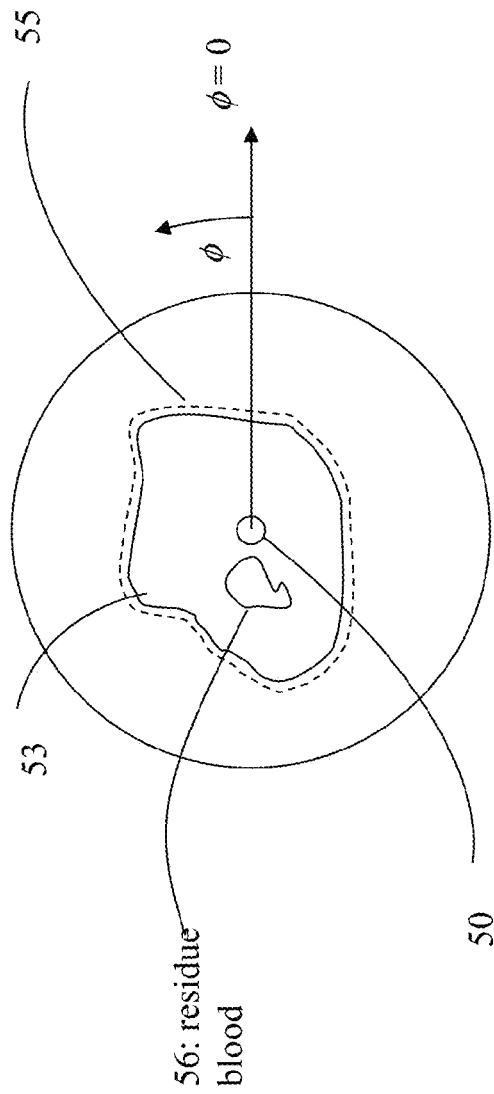
FIG. 4A shows a cross-section of a lumen with an imaging probe disposed therein according to an embodiment of the invention.

As shown in FIG. 4A, a probe 50 suitable for collecting OCT data is shown in the cross-section. During in vivo OCT imaging, the light beam travels through many catheter sheath layers and liquid layers (such as saline or flushing agent) before arriving at the vessel walls. These layers may introduce a certain amount of attenuation that cannot be well predicted. If the light impinges onto the tissue at an oblique angle, part of its intensity may be lost in the surface reflection. As shown in the figure, a lumen boundary 53 is shown relative to a superficial layer 55. The superficial layer 55 includes tissue a few coherence lengths away from the lumen boundary in the depth dimension is segmented. The region between the lumen boundary (the inner solid line) and the dotted line is the "superficial layer". ϕ is the rotational angle of the probe.

To correct for these effects, if the superficial layer 55 and other biological samples are composed of a homogeneous layer of fibrous tissue beneath the lumen boundary, it is reasonable to use the superficial layer 55 as a calibration basis for the ϕ dependence in A(z,ϕ). To do this, the boundary 53 between the lumen and the vessel is found either by manual selection or by an automatic program. The OCT intensity in the region is then averaged over the depth to give the angular-dependent intensity profile shown in FIG. 4B. In addition, FIG. 4B shows the angular-dependent intensity profile as a function of ϕ obtained from the superficial layer.

Figure 4B:
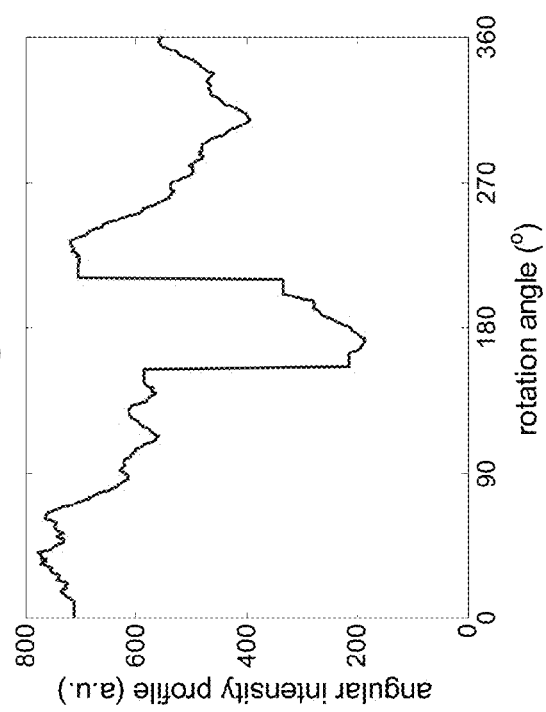
FIG. 4B shows an exemplary angular intensity profile with respect to rotational angle of the probe according to an embodiment of the invention.

The inverse of this profile shown in FIG. 4B is applied to OCT signal. The application of the inverse profile corrects the rotation-dependent intensity variation and non-uniform blood attenuation in the lumen. For example, applying such an inverse profile to an OCT image would yield the image shown in FIG. 4A. In general various profiles and models are used to improve OCT image quality as described herein. Another problem with tissue characterization arises due to unwanted noise which makes it more challenging to distinguish tissue boundaries and distinguish other regions of interest.

Figure 5B:
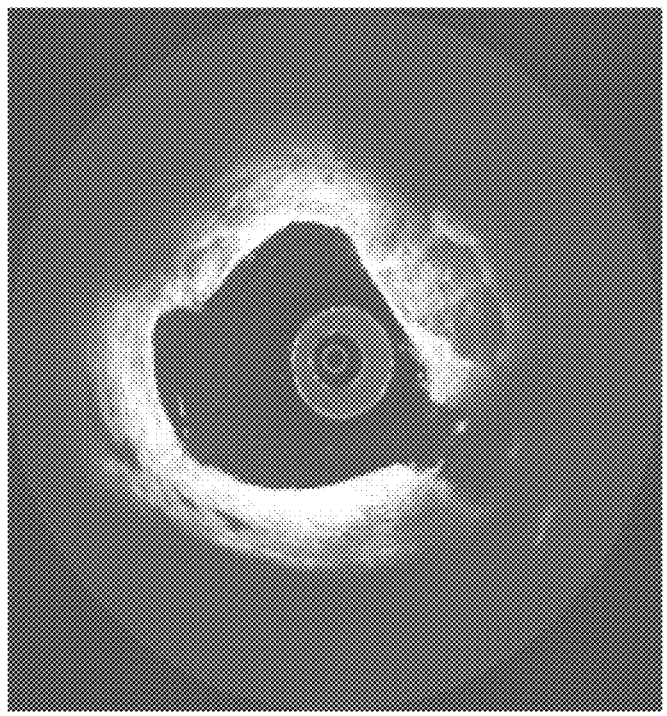
FIGS. 5A-5B illustrates the results from the application of an exemplary method of OCT image denoising according to an illustrative embodiment of the invention.
Figure 5A:
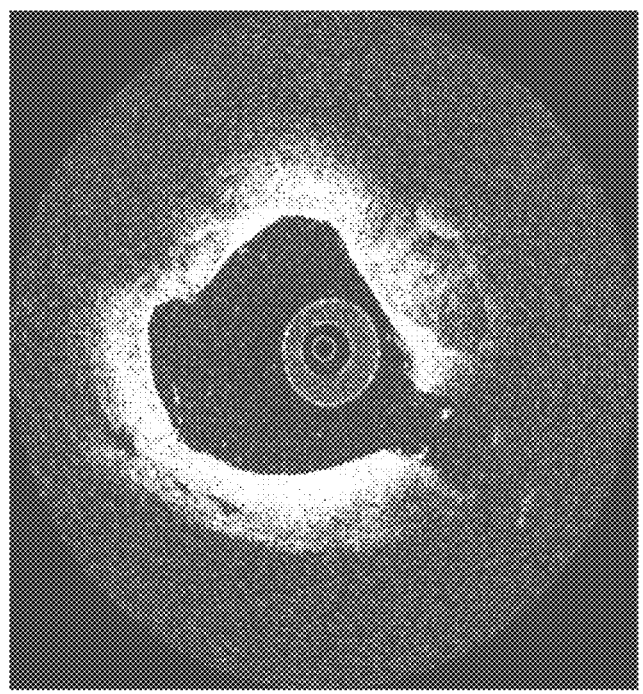

OCT image noise has several components: shot noise, laser noise and electrical noise. OCT images are also degraded by speckles. The speckle effect is inherent to coherent imaging and can reduce the accuracy of measurements of optical properties. To maintain high-resolution accuracy, denoising procedures that remove noise without degrading spatial resolution are performed. FIG. 5A shows a "before" image while FIG. 5B shows an improved "after"

image following the application of the denoising procedures. Suitable denoising techniques and algorithms are known to those skilled in the art.

Figure 6A:
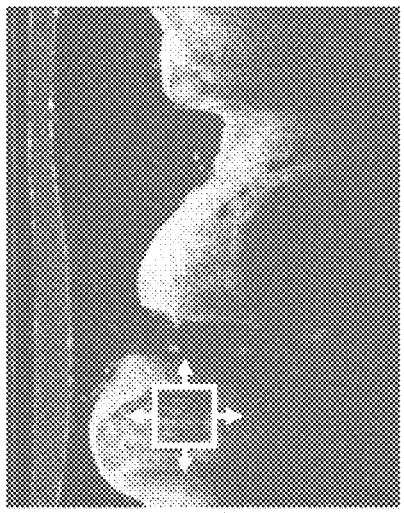
FIG. 6A illustrates OCT scan data being processed using a window as part of a method for optical property extraction according to an embodiment of the invention.
Figure 6B:
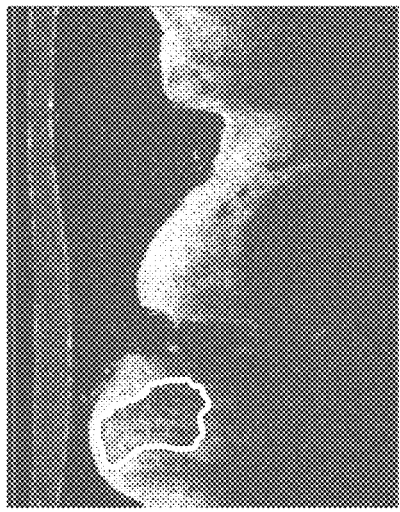
FIG. 6B illustrates OCT scan data being processed to define a region of interest according to an embodiment of the invention.
Figure 6C:
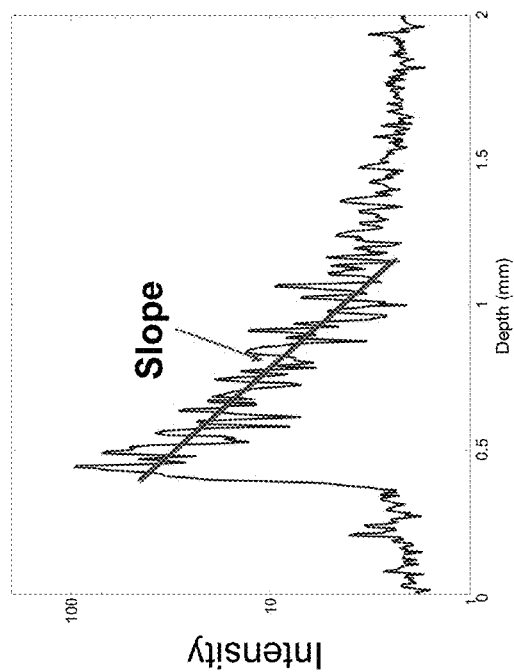
FIG. 6C is data plot with a linear portion used to model certain optical properties from a set of OCT data according to an embodiment of the invention.

As shown in FIG. 6A, in one embodiment of this invention, a window W of image data of an appropriate size is taken. This window can be moved as shown in FIG. 6A to select different regions of interest over time (see FIG. 6B, $ROI_A$). Alternatively, the window W can be resized. In one embodiment, where no human interaction or automatic segmentation method is required, a window refers to a one, two, or three-dimensional point, region, or volume of a specified size. This window W is sized such that the enclosed region offers sufficient amount of data for reliable model-fittings while maintaining sufficient spatial resolution. The axial lines (points, planes, or other elements) in the window W are averaged to produce a depth profile (or other profile) for that window. Model fitting is applied to the depth profile to obtain optical properties corresponding to that data window. For example, if a single-scattering model is employed, the depth profile is scaled as logarithmic as shown in FIG. 6C to facilitate a linear model fit. Then a line fitting is applied to the profile. Based on Equation (1.1) the offset of the line fitting offers a measurement of the backscatter coefficient, while the slope offers a measurement of the attenuation coefficient.

Once an initial data set as been collected, the window W is then moved inside the OCT image to obtain optical properties at different locations in the image (see arrows shown in FIG. 6A showing possible directions of window movement). In another embodiment, region of interest (such as $ROI_A$ for example) are drawn either by a human operator or by a processor-based computer program or other software module. An exemplary region of interest $ROI_A$ is shown in FIG. 6B. OCT data inside a region of interest, such as that shown in FIG. 6B, is averaged to produce a depth profile. In turn, the optical properties for the regions of interest are obtained by model fitting such as the linear data fitting shown in FIG. 6C.

Figure 7:
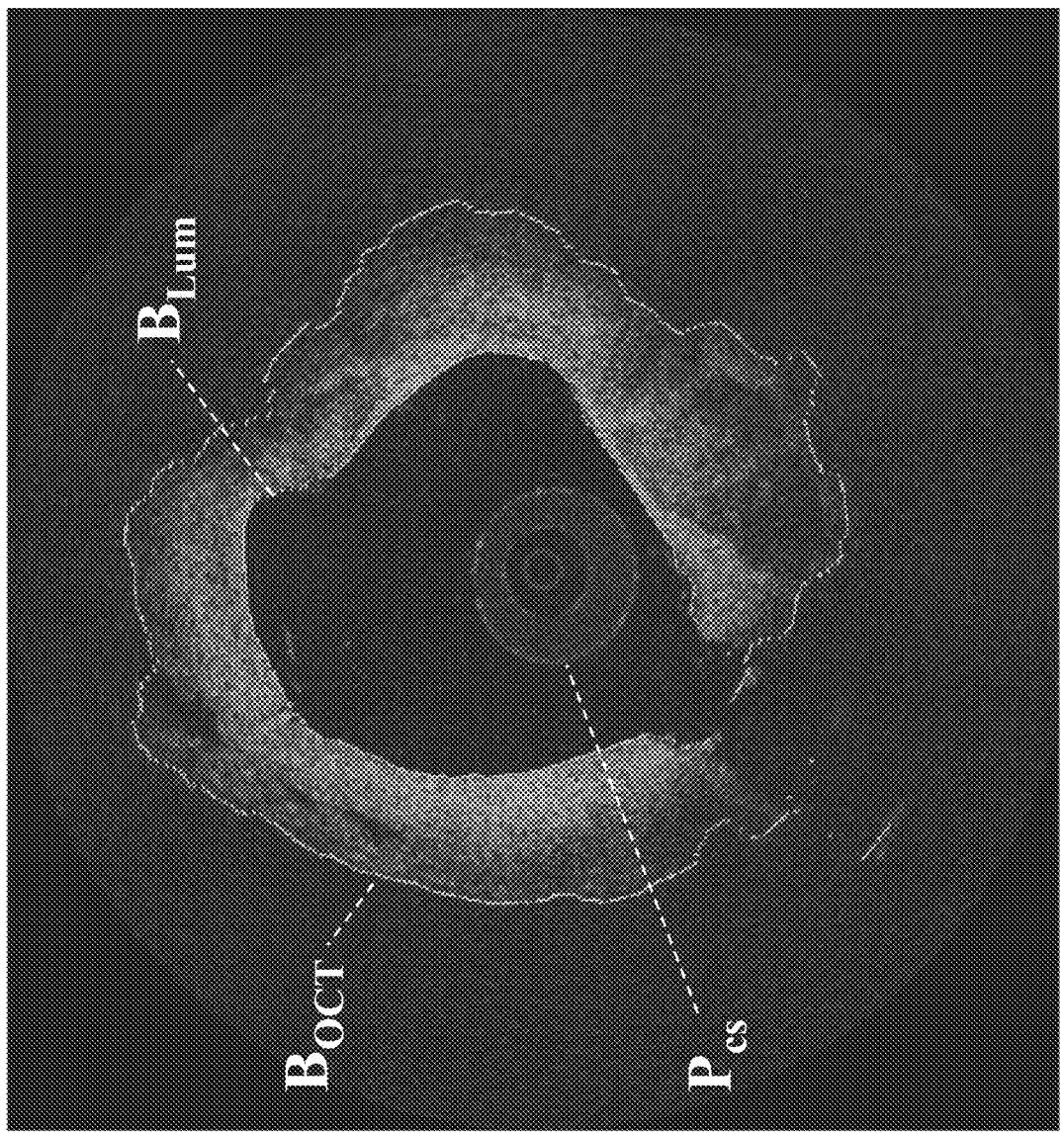
FIG. 7 illustrates a lumen cross-section and demonstrates the automatic detection of a lumen surface and an OCT penetration limit of interest according to an embodiment of the invention.

The wall of certain lumens, such as an artery, is a layered structure that includes different tissue components. In some embodiments, the linear model fitting shown in FIG. 6C is only accurate for a single lumen layer. Accordingly, to obtaining optical properties for regions of interest in a multi-layered structure, the lumen surface and the extent of the OCT penetration limit are first found by processing the OCT image or optical properties obtained from the OCT image. In one embodiment, this is performed by an automated computer program. In FIG. 7, the outer boundary $B_{OCT}$ shows the penetration limit of the OCT system. In contrast, the inner boundary of the lumen is show by the inner boundary $B_{Lum}$. A cross-section of the imaging probe $P_{cs}$ is also shown. As shown, the visibility of the outer boundary $B_{OCT}$ has been enhanced by the automated computer program.

Figure 8:
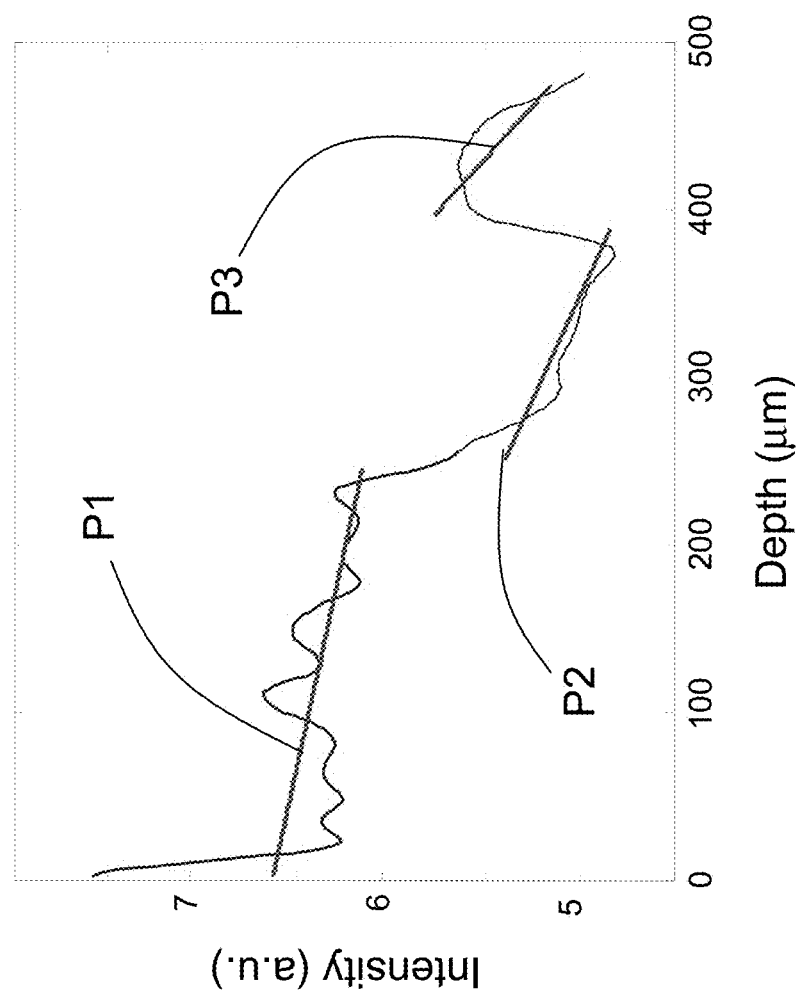
FIG. 8 illustrates a plotted OCT dataset suitable for performing tissue boundary localization using piece-wise regression on a one-dimensional OCT axial scan according to an embodiment of the invention.

In addition to analyzing a multi-layered structure and obtaining optical property data, the boundaries between different tissue types are also of interest. In one embodiment of this invention, the tissue boundary detection is obtained by analyzing a single depth scan. An example of such boundary detection can be understood using the illustrative OCT data plot and linear curve fitting model in FIG. 8. The depth profile is fitted with piece-wise model. As shown, although non-limiting, different linear portions (P1-P3) are shown. Once the piece-wise linearization is complete, such as shown in FIG. 8, the discontinuities or break-points denote the tissue boundaries, while each line segment denotes one tissue type. For example, in FIG. 8, P1 represents or corresponds to the fiber tissue, P2 represents or corresponds to calcification tissue, and P3 represents or corresponds to lipid tissue. The discontinuity between P1 and P2 shows a tissue boundary between the fiber tissue and the calcification tissue.

Figure 9:
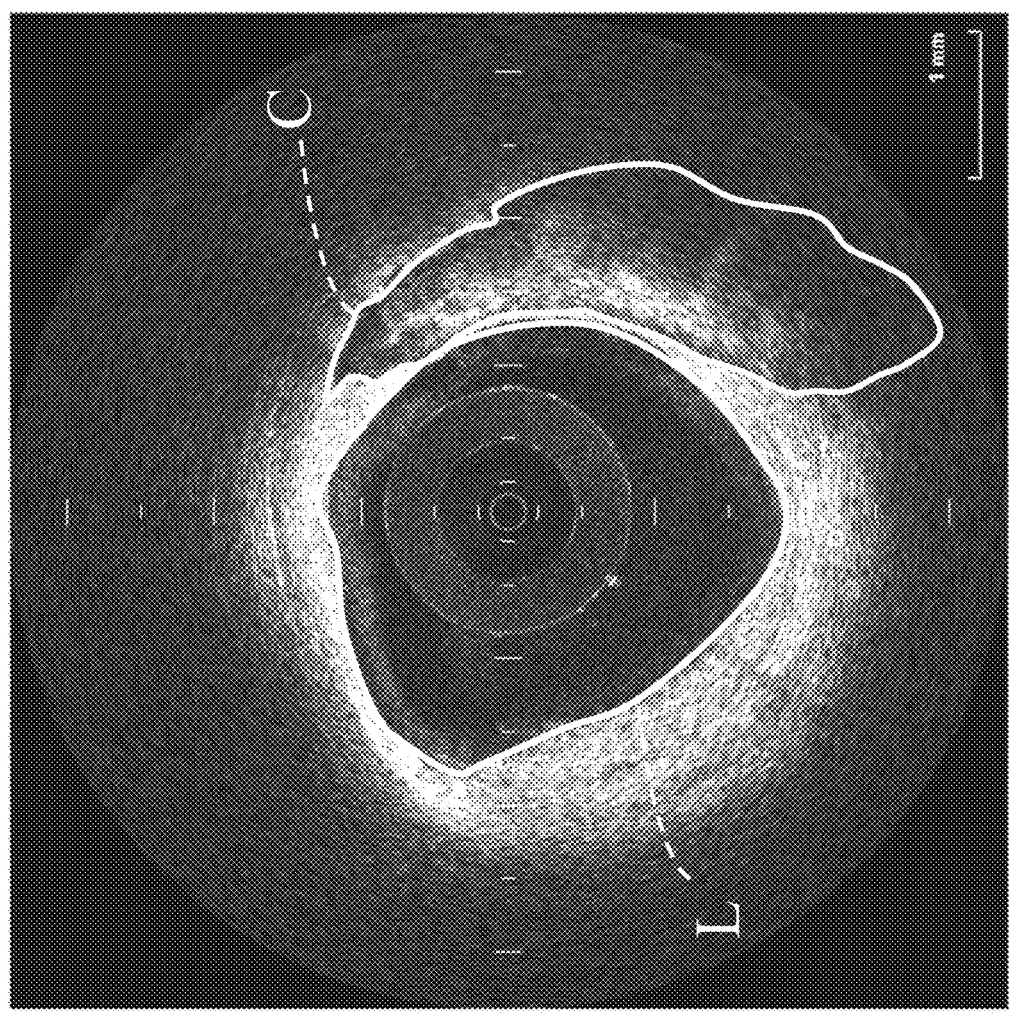
FIG. 9 illustrates a two-dimensional cross-section of a lumen obtained using an OCT scan such that the tissue boundary localization was generated using Canny's edge detector method.

In another embodiment of this invention, tissue boundary detection is obtained by analyzing 2D or 3D OCT images, either by a human operator or an automatic algorithm. An example of such boundary detection is illustrated in FIG. 9. As shown, a two-dimensional OCT image of a lumen is shown. The lumen L and calcification C boundaries are detected with automatic edge-detection methods, e.g., edge detection algorithm.

Once tissue boundary detection is complete, corrected optical properties are retrieved by computational models. One example of such a model compensates for backscattering by the amount of cumulative attenuation due to any layers between the region being scanned and the imaging catheter. For the hypothetical OCT image shown in FIG. 10A, first the tissue region Y is segmented by methods outlined above, which has different optical properties from the surrounding tissue region X. There may be up to N scan lines in the OCT images. Without loss of generality, two scan lines $S_1$ and $S_2$ can be considered. These two scan lines intersect with the lumen surface, the top boundary of tissue Y, and the bottom boundary of the tissue Y at $A_1$, $B_1$, $C_1$ and $A_2$, $B_2$, $C_2$, respectively. If the length of segment $A_1B_1$ and $A_2B_2$ is $d_1$, and $d_2$, respectively, the intensity profile of $S_1$ and $S_2$ are shown in FIGS. 10B and 10C, respectively. The slope $S_{X,i}$ and $S_{Y,i}$ of the intensity profile $S_1$ and $S_2$ are calculated in their respective regions, where subscript i denotes the different scan lines.

To reduce the effect of noise and speckle, the attenuation coefficients of tissue X and Y are then calculated as the average of the slopes of all scan lines. The backscattering coefficient of tissue X is calculated as the offset of the intensity profile between $A_i$ and $B_i$. However, because the attenuation effect of tissue X, the backscattering coefficients of tissue Y can not be calculated simply by the offset of the intensity profile between $B_i$ and $C_i$. Another approach is used. Specifically, the effect on the offset by the attenuation due to the tissue X on top of tissue Y can be compensated using the following equation:

$$O_{y,i}' = O_{y,i} + S_{x,i} d_i \ i=1,2,$$

In the equation above, the $O_{y,i}$ is the offset of the line fitting of tissue Y, $S_{x,i}$ is calculated from the line fitting of tissue X, $d_i$ is the thickness of tissue X. The $O_{y,i}'$ and $O_{y,i}$ are the compensated and the original offset of the line fitting at tissue Y, respectively. $S_{x,i}$ is the slope of the line fitting at tissue X and $d_i$ is the depth spanned by scan line inside tissue X.

To reduce the effect of noise and speckle, the backscattering coefficients of tissue X and Y are then calculated as the average of the compensated offsets of all scan lines, Although in the above example the hypothetical image has only two tissue layers, the method can be extended to multiple-layers OCT image by compensating the offsets of bottom layer iteratively from the top.

Another embodiment of this invention relates to the extraction of image features associated with specific tissue types based on 2D or 3D images. These features are not extracted solely from a depth-dependent scanning line, but rather rely on analysis of the patterns of neighboring scans. One example is differentiating calcium tissue and lipid tissue. In OCT, both tissue types appear to be signal poor while the surrounding fibrous or ground tissues appear to be signal rich. However, the boundary between calcium tissue and fibrous tissue is usually sharp, while the boundary between lipid tissue and fibrous tissue in OCT usually appears diffusive. The boundary sharpness can be quantified by measuring the derivative of the image brightness (edge acutance). Other quantifiable local image features include texture and shape information.

One semi-automatic method for measuring boundary sharpness requires the operator to roughly preselect an edge line or a small area enclosing the edge line. Edge detection algorithms (such as Canny's edge detector or region-growing methods) are then used to detect the precise location of the edges. The gray-level variance across the edge line yields a measure of the edge acutance. The edge acutance value is calculated by quantifying the inside-to-outside differences between the signals of the plaque and the surrounding tissue.

In computer vision, texture usually refers to patterns of local variations in brightness. In an OCT image, texture is closely related to the speckle formation, which is influenced by the density and size distribution of scattering elements or structures. In vessel imaging, under similar focusing conditions, the texture is observed to be correlated to tissue type. For example, large and densely packed macrophage foam cells form large speckles and exhibit a "solid" texture; while loosely packed proteoglycan molecules with smaller scattering elements form small speckles and exhibit a "gel" texture. There are numerous ways to quantify texture information in computer vision, including methods based on intensity statistics (histogram or variance), local pattern analysis (e.g., spatial gray-level co-occurrence matrices), or spectral analysis.

Different atherosclerosis plaques have different geometrical shapes. For example, the foam cells usually form ribbon-like features on the shoulders of large lipid pool. In turn, the media appears like annulus around the vessel, etc. The shape information is currently used in qualitative assessment of OCT images. In computerized shape analysis, compactness, Fourier descriptors, central invariant moment, and chord-length distributions are the most commonly used methods. It should be appreciated that shape information can be either 2D shape, 3D shape or both.

It should be appreciated that while optical backscattering coefficient, optical attenuation coefficient, image edge sharpness, image texture, image shape are described in detail above as tissue parameters, the present invention is not limited to these parameters. Thus, other parameters (such as optical anisotropic factor) are within the scope of this invention. It should also be appreciated that while models and calculation methods to derive the parameters described above are possible methods, there are other physical models or calculation methods that are within the scope of this invention.

Figure 11A:
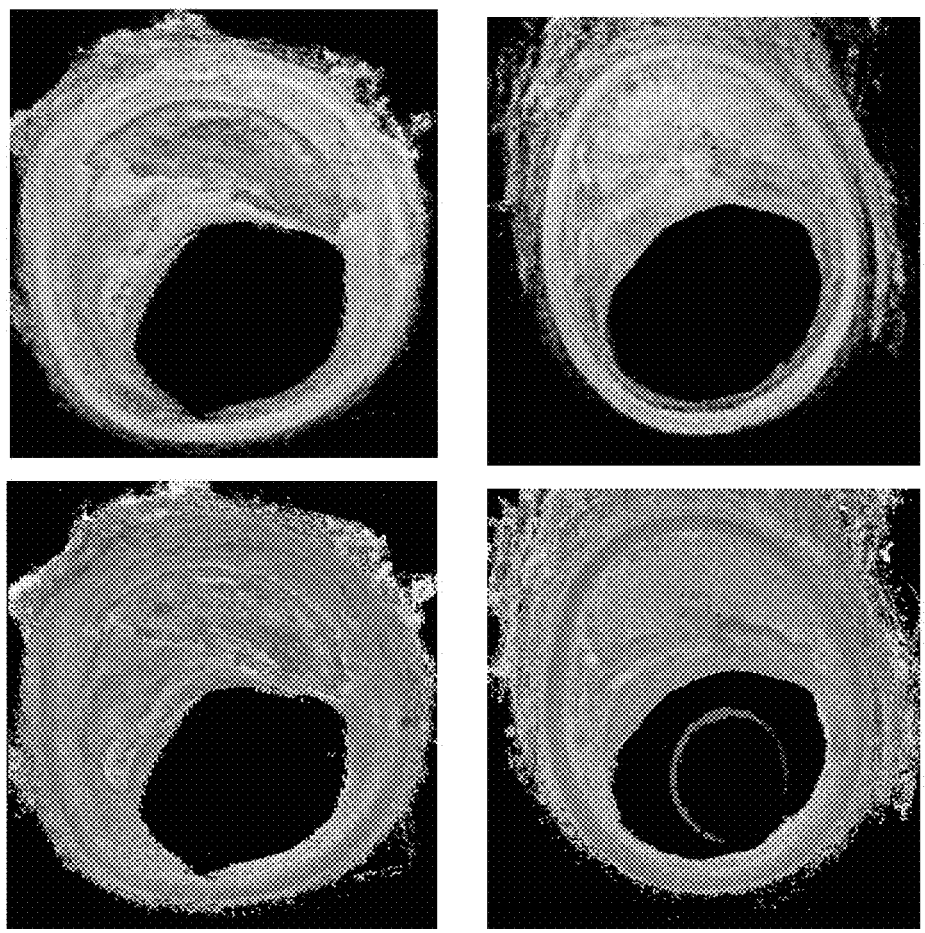
FIG. 11A includes four image data plots showing exemplary tissue characterization coefficients relating to backscattering and attenuation data according to an embodiment of the invention.

A quantitative measurement of optical tissue and image properties can be displayed to an OCT operator to assist in clinical interpretation. In one embodiment, the tissue properties are displayed individually. In another embodiment, multiple tissue properties are displayed together using a combination display method. For example, there are two tissue cross-sections shown in FIG. 11A. The attenuation coefficients and backscattering coefficients are shown individually using a grayscale mapping. FIG. 11B shows a combination display method where the color map is devised to combine the backscattering and attenuation measurements. Letter "C", "F", and "L" denote the positions of average backscattering and attenuation coefficients for calcification, fibrous and lipid tissue, respectively. FIG. 11C shows the images combining backscattering and attenuation measurements in FIG. 11A using the color-map defined in FIG. 11B. Because the figures are published in black-and-white, FIG. 11D and FIG. 11E are shown by replacing the color-map in FIGS. B and C with hatched texture maps. Improved contrast enhancement can be obtained using this approach to visualize plaques. It should be noted that instead of texture map, color-map or symbol encoded map using true colors or symbols can also be used and often generates improved visualizations.

In the another embodiment of the present invention, the characterization software analyzes the OCT data and measured tissue optical properties to generate image segmentations, define tissue boundaries, and identify tissue elements in samples of interest. The tissue parameters are calculated for each tissue sample or element thereof and compared to the parameters stored in a database. Based on these results, the tissue type or characterization is assigned to the tissue sample of element thereof according to univariate or multivariate discriminant analysis or classification. In one embodiment, the calculated tissue parameters are displayed as numbers or color-coded images (e.g., discrete colors, grayscale, etc.). In another embodiment, the derived tissue types are displayed to the user as texts or color-coded images (e.g., discrete colors, grayscale, etc.). These features are described below in more detail.

Figures 12A, 12B:
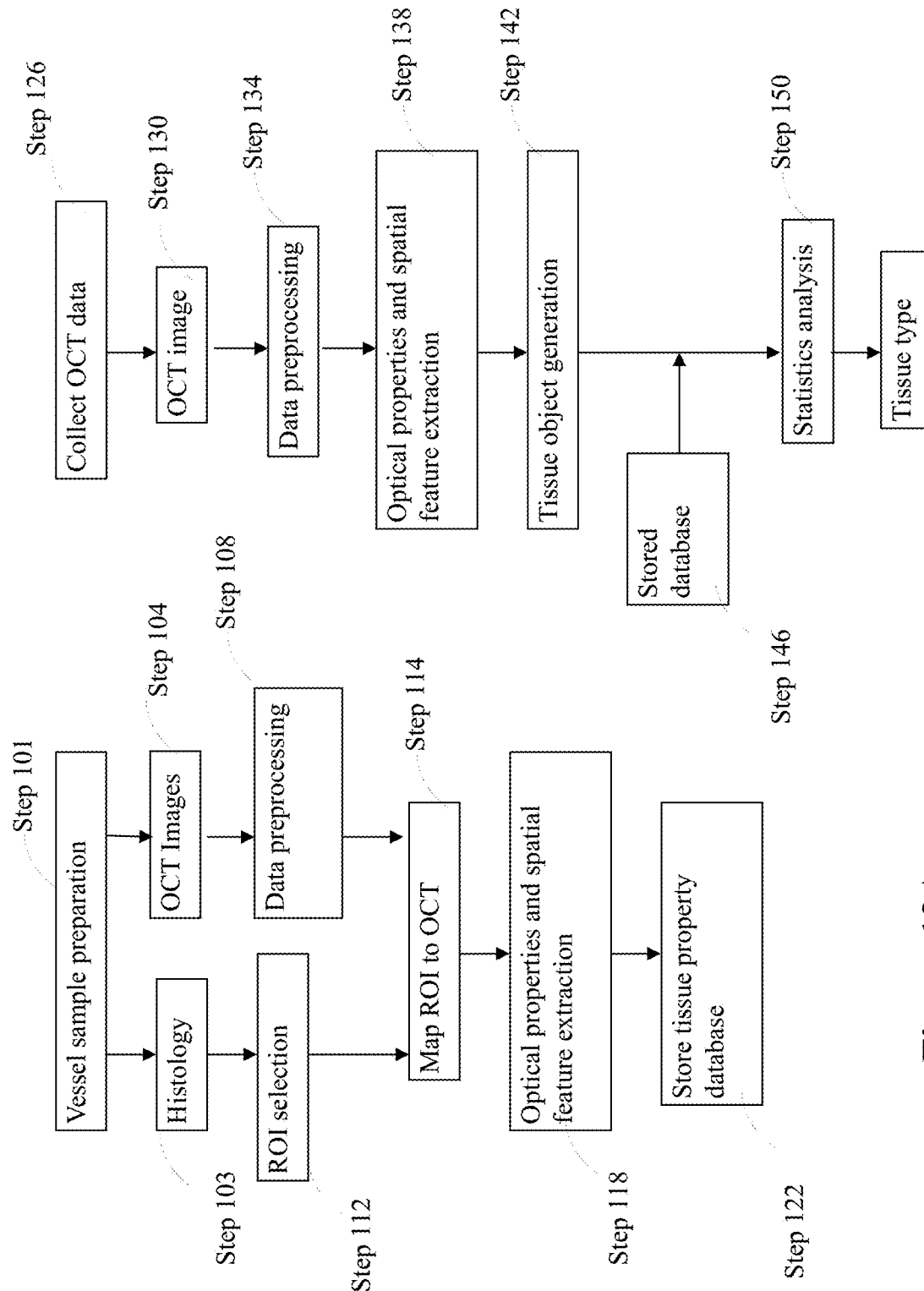
FIGS. 12A and 12B illustrate, respectively, methods of tissue characterization by histological preparation and OCT data processing in accordance with embodiments of present invention.

Another method of generating and analyzing quantitative measurement of tissue optical and image properties is shown in FIGS. 12A and 12B. In one embodiment, two major phases can be used. The first phase is an analysis and database populating phase and the second phase is a tissue characterization phase for a patient. These phases can be performed using the database and software shown in FIG. 1.

As shown in FIG. 12A, in the database populating phase, the vessel samples are excised and prepared (step 101) and OCT data is collected from a portion of the vessel. The histology data (step 103) and OCT data (step 104) are collected in parallel as shown. In one embodiment, the OCT data is calibrated and the artifacts removed to generate consistent measurement. In one embodiment, data-preprocessing steps (step 108) are performed. The data-preprocessing steps can include, but are not limited to calibrating the system power, correcting a focusing effect, correcting angular dependence, and de-noising steps described in text above and in FIGS. 2, 3, 4, 5. The interrogated portion of the vessel is sectioned and processed by standard histology processing. Regions of interest encompassing specific tissue type (or vessel characterization) are identified by operator or a machine using certain criteria (Step 112). The regions of interest are mapped (step 114) to the OCT image data or processor-generated OCT image. Optical properties and spatial feature extraction (step 118) can also be performed. Finally, any resolved tissue properties can be stored (step 122) in a database for future analysis.

Similarly, FIG. 12B shows a method of identifying tissue type in situ. This method includes the step of collecting OCT data (step 126). Once collected, this OCT data is used to generate an OCT image (step 130) with respect to the scanned lumen or other sample of interest. In one embodiment, the OCT image is then subjected to the data-preprocessing steps (step 134). Optical properties and spatial feature extraction (step 138) can then be performed as outlined above. Tissue type identifiers or signatures are generated (step 142) as discussed above. Next, any suitable tissue type identifiers or signatures are stored (step 146) in the relevant database. At this point, various types of statistical analysis (step 150) as described herein can be performed to identify a particular tissue type in the OCT image using the stored tissue type identifiers or signatures.

Figure 13A:
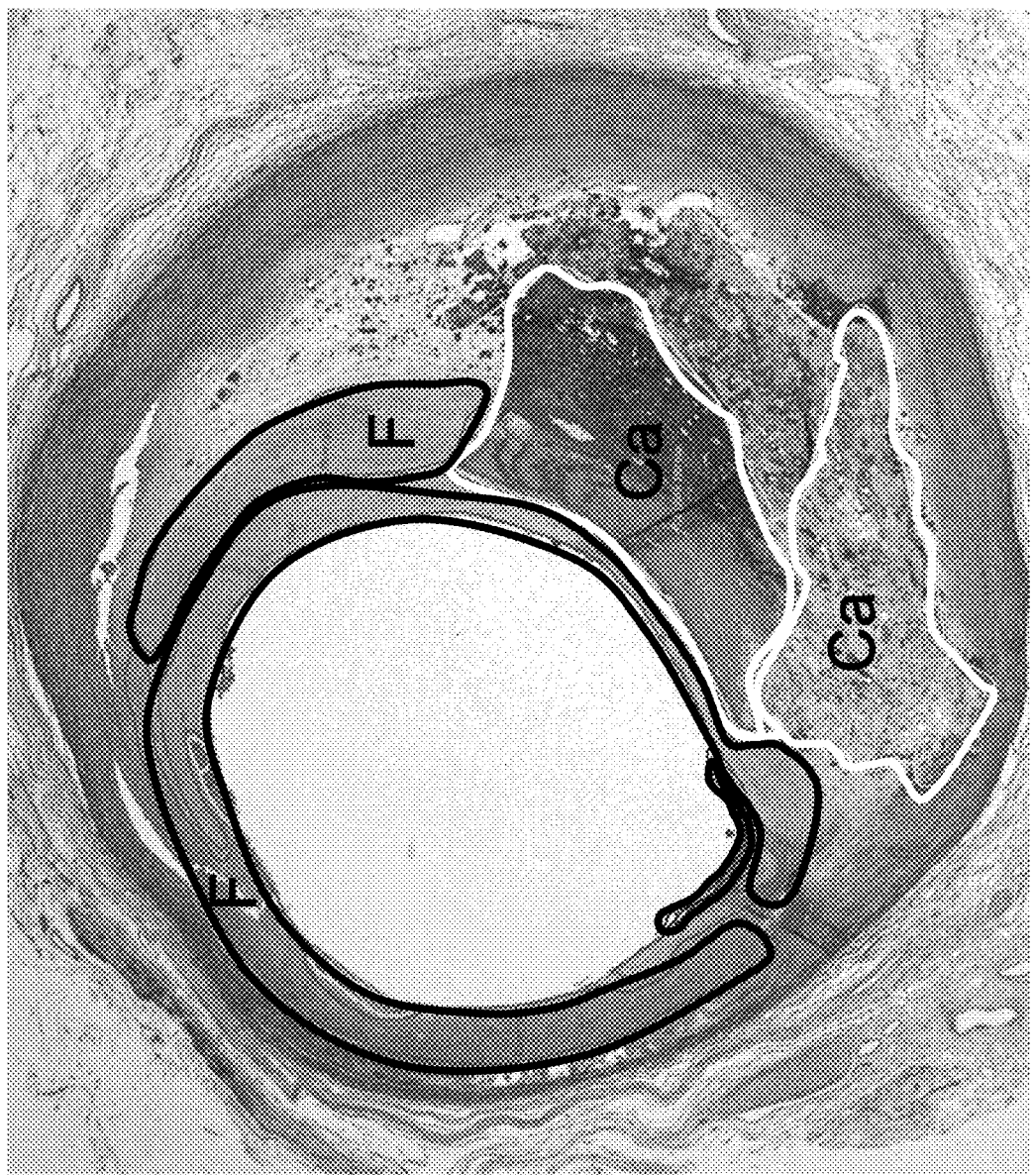
FIG. 13A shows an example histology image with mapped tissue types according to an embodiment of the invention.
Figure 13B:
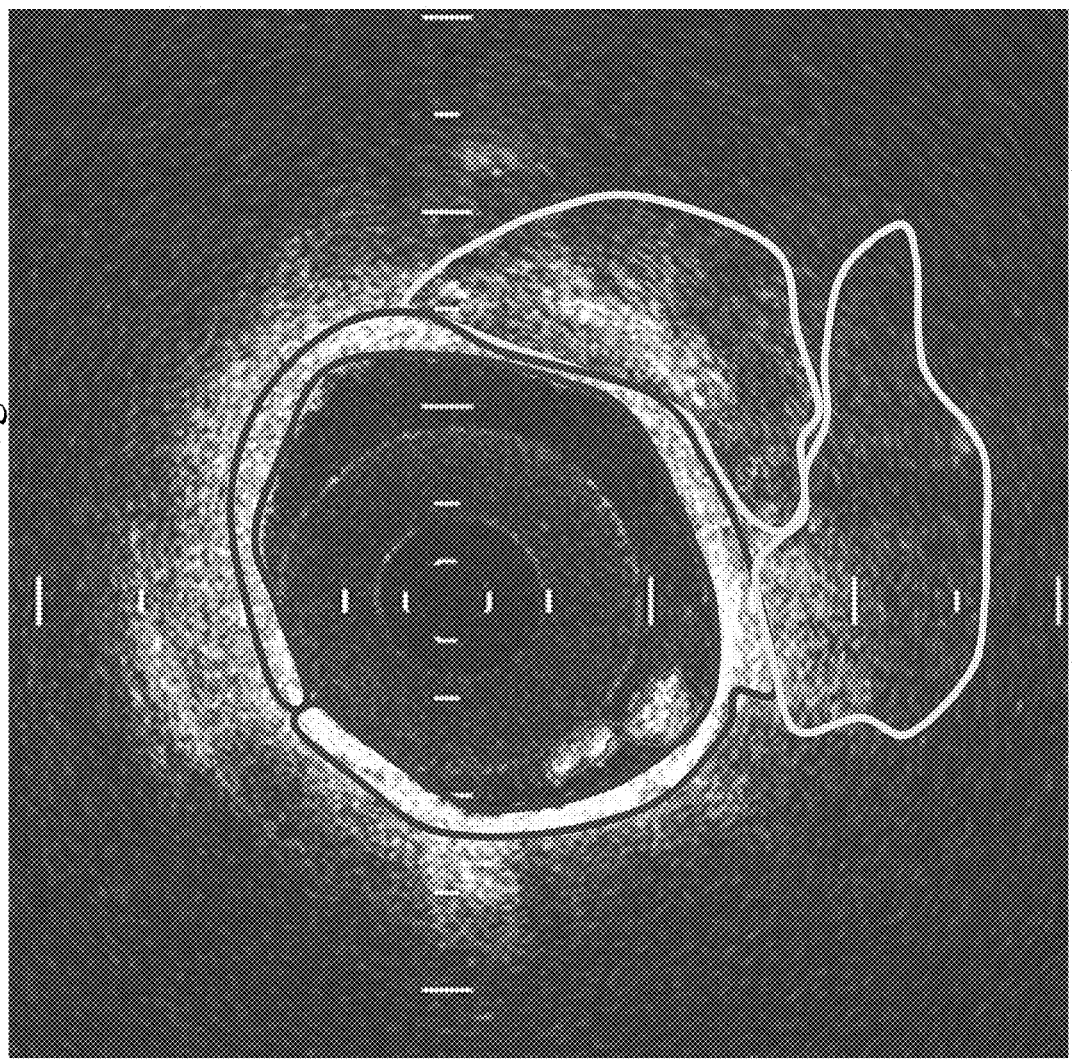
FIG. 13B shows an OCT image in which the tissue types and data identified in FIG. 13A have been mapped and identified with boundaries according to an embodiment of the invention.

During database population phase, different tissue types are identified and mapped on the histology images. These tissue identifiers or signatures that are stored can be used in the future to automatically identify tissue elements and types of interest for new OCT scans. The corresponding regions are also identified in the OCT data or image. An example of such mapped histology images is shown in FIG. 13A where tissue types (e.g., fibers ("F"), calcification ("Ca"), etc) were identified. The corresponding mapped OCT image is shown in 13B. At least one optical property and other image features are extracted and stored in a tissue property database. The above-described process is repeated for each tissue types and each characterization as many times as desired to increase the accuracy of the quantitative measurement of parameters.

Figure 14:
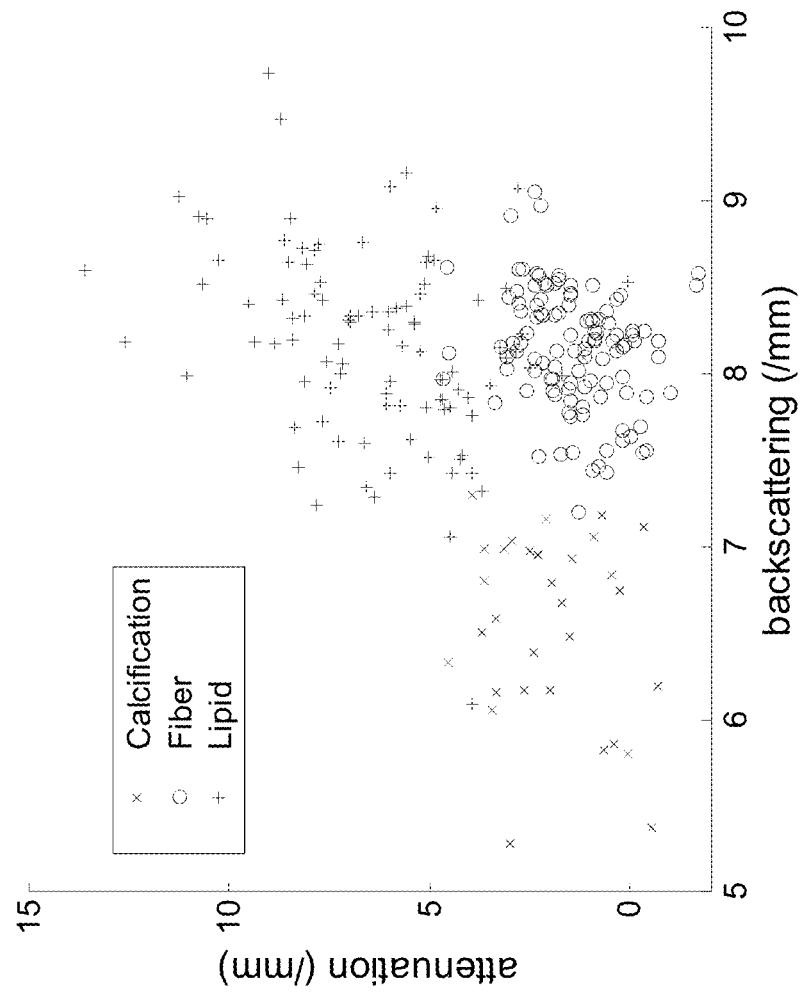
FIG. 14 shows a plot of attenuation data versus backscattering data with respect to certain tissue properties obtained from real human atherosclerosis plaques using methods described in FIGS. 12A-12B.

An example of suitable data for use in the database is shown in FIG. 14, where the attenuation and backscattering coefficients for three tissue types are plotted. As shown in the plot, the calcification, fiber and lipid tissue forms clusters that are distinguishable by their positions in attenuation/backscatter space, which is the basis for the tissue characterization. In the tissue characterization phase, the vessel to be interrogated is imaged with OCT. The image is calibrated and the artifacts are removed. Then regions of interest are generated either by operator input or by automatic segmentation algorithm. The optical properties and other image features are extracted from the regions of interest. The quantitative measurements are compared to the tissue property database generated in the first phase.

There are many statistical methods to compare the tissue properties of a ROI to the database and to assign the tissue type. In one embodiment of this invention the discriminant analysis method (or classification analysis method) is used to identify tissue types based on the tissue properties. For example, different tissue types have different the optical backscattering $\mu_b$ and the attenuation coefficient $\mu_a$. For any ROI to be examined, both parameters are measured. Hence, during the database population phase, the ($\mu_b$, $\mu_a$) pairs of different tissue types are obtained.

Figure 15A:
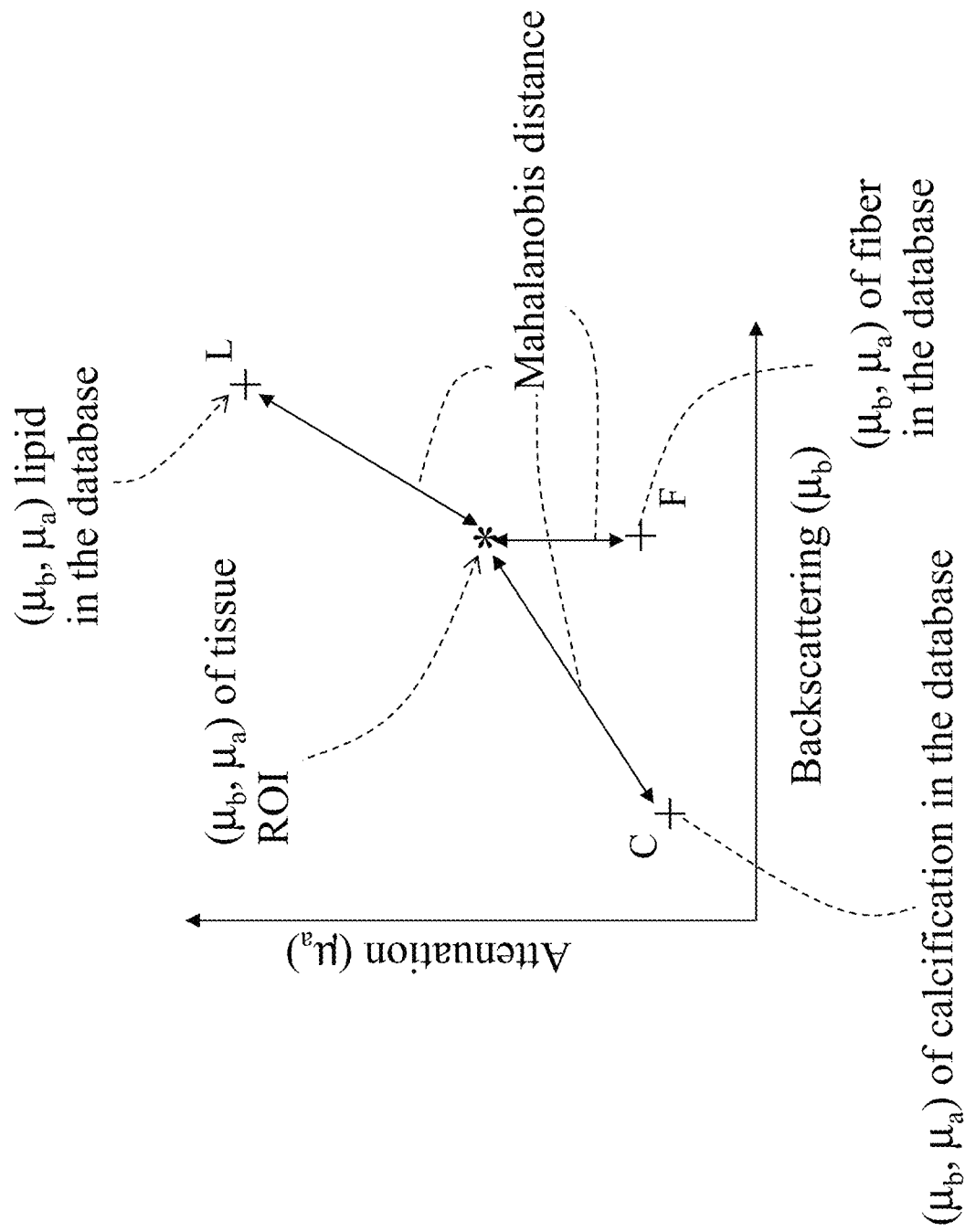
FIG. 15A shows a plot of attenuation data versus backscattering data suitable for use with a tissue characterization discriminant method that compares the tissue properties of region of interest to the tissue properties populated in a database.
Figure 15B:
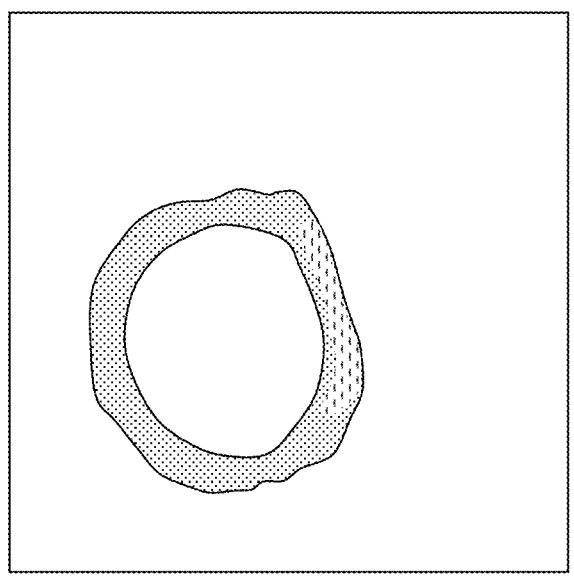
FIG. 15B illustrates an exemplary OCT tissue characterization image in which a computer texture overlay is used to describe regions of interest according to an embodiment of the invention.

During characterization phase, the ($\mu_b$, $\mu_a$) pair of the tissue ROI is obtained, and the Mahalanobis distance is calculated between those of new acquired ROI and those values from the database. From the calculation, a decision is made to find the best match. For example, as shown in FIG. 15A, the distance is shortest between the ROI to the fibers in the database, and the ROI is characterized as fibrous tissue with a certain amount of confidence. The characterization results can be displayed as color-coded image or displayed using text legends describing the possible tissue characterization. FIG. 15B is an example of such characterization, where the overall gray dotted region represents the fibrous region, while the bottom "-" dotted region represents the lipid region. The different color-coded or selectively marked tissue regions and the associated coded legends, include but are not limited to a fiber, lipid pool, fibrofatty, calcium nodule, calcium plate, calcium speckled, thrombus, foam cells, proteoglycan, and others. FIG. 15B and FIG. 11C are related, but different. In FIG. 15B the tissue types are pre-classified for the clinicians, while in FIG. 11C, a contrast-enhanced image is displayed, but the decision of tissue type is made by clinicians when interpreting the image.

It should also be noted that the optical properties and image features for such discriminant or classification analysis are not limited to backscattering coefficients and attenuation coefficients, but include, although not limited to edge sharpness, texture parameters, plaque geometrical shape etc. In addition, the algorithms for performing such analysis are not limited to Mahalanobis distance analysis, but include a variety of statistical methods. Biological tissues are complex. There are many tissue types and sub-types that possibly could not be distinguished by only combining the backscattering and attenuation measurements. For example, the foam cell tissue, and the lipid both have high backscattering and attenuation. Calcification and certain loose connective tissue both have low backscattering and low attenuation. In addition, there are often some overlaps for backscattering and attenuation measurements between different tissue types. For example, some large calcified plaques have small lipid or fibrous tissue pockets embedded inside, hence having higher backscattering coefficients. In these cases, it is often necessary to make additional optical or image parameters to assist or refine tissue characterization.

Figure 16A:
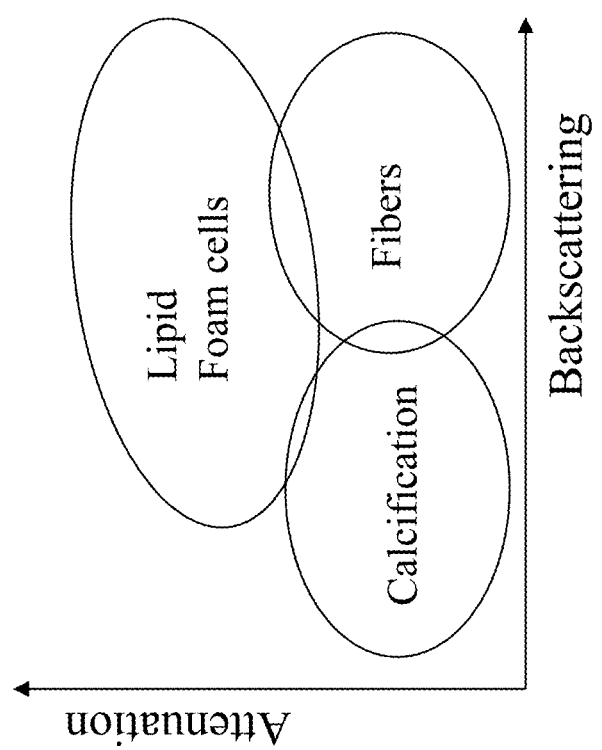
FIG. 16A is a plot depicting the backscattering vs. attenuation data shown in FIG. 14 according to an embodiment of the invention.

Additional parameters may be used for assisting and refining tissue characterization. In FIG. 16A is a plot summarizing the backscattering vs. attenuation plot shown in FIG. 14. There are significant overlaps between calcification to the lipid/foam cells tissue. The lipid tissue and foam cell tissue also have similar properties. Therefore, a discriminant method based on this plot alone is not sufficient to distinguish these tissue types with high accuracy.

Figures 16B, 16C:
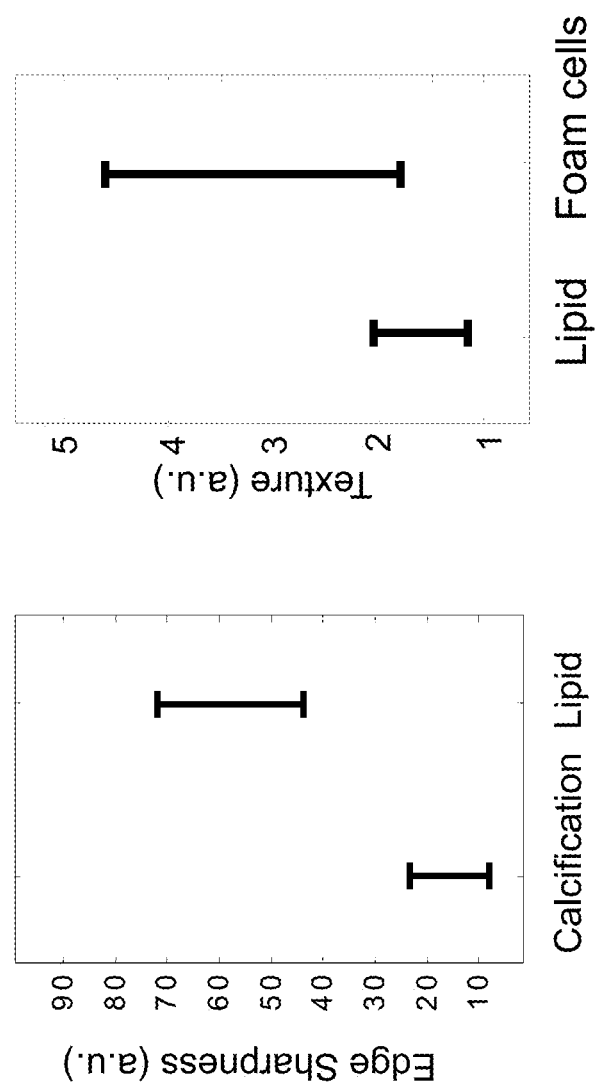
FIGS. 16B-16C are plots depicting edge sharpness and texture, respectively, as measured for a boundary of interest according to an embodiment of the invention.

FIG. 16B shows a plot of edge sharpness measured for the boundary formed by the calcification tissue and fibrous tissue, and the boundary formed by the calcification tissue and lipid tissue. Significant difference was found for the edge transition width between these two types of boundaries. Hence, FIG. 16B could be used to further refine the tissue classification.

In OCT coronary artery imaging, foam cells are also an important indicator of disease state. The foam cells are usually enlarged macrophage or smooth muscle cells that are filled with lipid droplets. Because of the presence of these lipid droplets, it is often difficult to distinguish them from some lipid tissues. However, because foam cells are large cells and are often clustered into groups of various size, they tend have different texture appearance from lipid tissues, which are usually composed of extracellular lipid.

FIG. 16C shows a texture parameter, gray-level co-occurrence matrix for lipid and macrophage tissue. The gray-level co-occurrence matrix calculation is available in many standard commercial image processing software, such as Matlab (MathWorks, Natick, Mass.). Although there are still some overlap between the lipid and foam cells in terms of texture measurements, the additional information helps to improve tissue characterization accuracy.

The above analysis is to analyze edge sharpness and texture measurements after analyzing backscattering and attenuation. In other embodiments all of the analysis and comparison can be performed in parallel or in a combination serial/parallel steps. The data and decision shown in FIG. 16 is an example and additional parameters and threshold can be used with an OCT system trained using histology data as discussed above to identify any suitable tissue of interest.

Non-Limiting Software Features and Embodiments for Implementing OCT Methods and Systems The present invention may be embodied in may different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, histology images, OCT images, ROIs, overlays, signal processing, artifact removal, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, clock signals, region of interest types, formulas, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

What is claimed is:

1. A method of analyzing and imaging a blood vessel, the method comprising:
   storing image data of the blood vessel, in an electronic memory device, wherein the image data is generated using an imaging probe;
   generating one or more images of the blood vessel, using a computing device, from the image data, wherein the one or more images comprises one or more portions of a wall of the blood vessel;
   detecting a lumen boundary, using the computing device, with regard to the one or more images;
   detecting a tissue boundary, using the computing device, with regard to the one or more images, wherein the tissue boundary defines a region of tissue having a single tissue type, and wherein detecting the tissue boundary comprises identification of a profile of intensity versus corresponding depth in the blood vessel from the image data, and identification of one or more discontinuities in a linearization of the profile of the intensity versus corresponding depth;
   determining the tissue type, using the computing device; and
   displaying, using a display in electrical communication with the computing device, a first image from the one or more images, wherein the display of the first image includes adding a first visual representation of the tissue boundary shown in the first image and a second visual representation of the single tissue type relative to the first image.

2. The method of claim 1, wherein the tissue type is a tissue comprising calcium.

3. The method of claim 1, wherein the second visual representation are selected from a group consisting of an overlay, a colormap, a color, a texture map, and text.

4. The method of claim 1, wherein determining the tissue type comprises performing a statistical discriminant analysis of region of the one or more images within the tissue boundary.

5. The method of claim 1, wherein the tissue type is selected from the group consisting of cholesterol, fiber, lipid, fibrofatty, red thrombus, white thrombus, foam cells, and proteoglycan.

6. The method of claim 1, further comprising populating a database with histology data collected in parallel with collection of image data; and determining the tissue type using the populated database.

7. The method of claim 1, wherein the first visual representation of the tissue boundary is based on the one or more discontinuities.

8. The method of claim 1, wherein the imaging probe is a rotatable optical coherence tomography probe that is disposed in and pulled back through a lumen of the blood vessel.

9. The method of claim 8 further comprising correcting a focusing effect of imaging probe to improve tissue type determination, wherein the rotatable optical coherence tomography probe comprises a lens to send and receive light.

10. The method of claim 8 further comprising rotating the imaging probe and applying an angular intensity correction to account for an attenuation effect.

11. The method of claim 8, wherein the image data comprises backscattering data.

12. The method of claim 11 further comprising comparing the backscattering data to a first threshold, the backscattering data mapping to a first location in the one or more images; and if the backscattering data exceeds the first threshold, characterize the first location in the one or more images as having a first tissue characteristic.

13. The method of claim 8, wherein the image data comprises backscattering data and attenuation data.

14. The method of claim 13 further comprising determining the tissue type at a location in the blood vessel corresponding to an image location in one of the one or more images in response to the attenuation value and backscattering value at the image location.

15. The method of claim 13 further comprising measuring an attenuation value and a backscattering value at a point in the blood vessel, wherein the point is within the tissue boundary.

16. The method of claim 15 further comprising determining the tissue type at the point in response to the measured attenuation value and backscattering value.

17. The method of claim 13, wherein determining the tissue type further comprises generating a backscatter-attenuation space.

18. The method of claim 17, wherein determining the tissue type further comprises mapping a pair of coordinates in the backscatter-attenuation space to the second visual representation of a value of the pair of coordinates in the backscatter-attenuation space.

19. The method of claim 13 further comprising determining backscattering coefficients and attenuation coefficients from the backscattering data and attenuation data.

20. The method of claim 19, further comprising plotting pairs of backscattering coefficients and attenuation coefficients; and determining different tissue types based on clusters formed in the plot of such pairs.

* * * * *